(12) United States Patent
Benichou et al.

(10) Patent No.: US 8,795,354 B2
(45) Date of Patent: Aug. 5, 2014

(54) LOW-PROFILE HEART VALVE AND DELIVERY SYSTEM

(75) Inventors: Netanel Benichou, D.N. Hof Hacarmel (IL); Stanton J. Rowe, Newport Beach, CA (US); Sean Chow, Tustin, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 392 days.

(21) Appl. No.: 13/040,896

(22) Filed: Mar. 4, 2011

(65) Prior Publication Data

US 2011/0218619 A1 Sep. 8, 2011

Related U.S. Application Data

(60) Provisional application No. 61/311,165, filed on Mar. 5, 2010.

(51) Int. Cl.
*A61F 2/24* (2006.01)

(52) U.S. Cl.
USPC ......................................................... 623/2.11

(58) Field of Classification Search
USPC ........... 623/2.11, 2.14, 2.17, 2.18, 1.24, 1.26, 623/1.11, 1.12; 606/108
See application file for complete search history.

(56) References Cited

U.S. PATENT DOCUMENTS

| | | |
|---|---|---|
| 3,409,013 A | 11/1968 | Berry |
| 3,472,230 A | 10/1969 | Fogarty et al. |
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |

(Continued)

FOREIGN PATENT DOCUMENTS

| | | |
|---|---|---|
| DE | 19546692 | 6/1997 |
| DE | 19857887 | 7/2000 |

(Continued)

OTHER PUBLICATIONS

Andersen, et al., "Transluminal implantation of artificial heart valves. Description of a new expandable aortic valve and initial results with implantation by catheter technique in closed chest pigs." European Heart Journal (1992), 13, 704-708.

(Continued)

*Primary Examiner* — Corrine M McDermott
*Assistant Examiner* — Christopher L Templeton
(74) *Attorney, Agent, or Firm* — Klarquist Sparkman, LLP

(57) ABSTRACT

Disclosed replacement heart valves can be designed to be delivered to a native valve site while crimped on a delivery catheter. The crimped profile of the replacement valve can be minimized by, for example, separating a frame or stent structure from a leaflet structure, along the axial direction. Disclosed replacement valves can be transitioned from a delivery configuration, in which the crimped profile can be minimized, to an operating configuration. The replacement valve can be fully assembled in both the delivery and operating configurations. In some embodiments, the leaflets can be positioned outside of the stent in the delivery configuration, and positioned inside of the stent lumen in the operating configuration. Disclosed replacement valves can include a flexible sleeve coupling the leaflets to the stent and facilitating the transition to the operating configuration. Methods of implanting said replacement valves are also disclosed.

14 Claims, 14 Drawing Sheets

(56) References Cited

U.S. PATENT DOCUMENTS

| | | |
|---|---|---|
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,000 A * | 7/1989 | Gupta ............ 623/2.18 |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane et al. |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely |
| 5,554,185 A | 9/1996 | Block et al. |
| 5,571,175 A | 11/1996 | Vanney et al. |
| 5,591,185 A | 1/1997 | Kilmer et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,042,607 A | 3/2000 | Williamson, IV et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasakaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian |
| 6,302,906 B1 | 10/2001 | Goecoechea et al. |
| 6,350,277 B1 | 2/2002 | Kocur |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,569,196 B1 | 5/2003 | Vesely et al. |
| 6,582,462 B1 | 6/2003 | Andersen et al. |
| 6,605,112 B1 | 8/2003 | Moll |
| 6,730,118 B2 | 5/2004 | Spenser et al. |
| 6,733,525 B2 * | 5/2004 | Yang et al. ............ 623/2.18 |
| 6,830,584 B1 | 12/2004 | Seguin |
| 6,893,460 B2 | 5/2005 | Spenser et al. |
| 6,908,481 B2 | 6/2005 | Cribier |
| 7,018,406 B2 | 3/2006 | Seguin et al. |
| 7,276,078 B2 | 10/2007 | Spenser et al. |
| 7,276,084 B2 | 10/2007 | Yang et al. |
| 7,374,571 B2 | 5/2008 | Pease et al. |
| 7,381,219 B2 | 6/2008 | Salahieh et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,530,995 B2 * | 5/2009 | Quijano et al. ............ 623/1.24 |
| 7,585,321 B2 | 9/2009 | Cribier |
| 7,597,711 B2 * | 10/2009 | Drews et al. ............ 623/2.11 |
| 7,618,446 B2 | 11/2009 | Andersen et al. |
| 7,708,775 B2 * | 5/2010 | Rowe et al. ............ 623/2.11 |
| 7,947,072 B2 * | 5/2011 | Yang et al. ............ 623/1.26 |
| 7,981,153 B2 * | 7/2011 | Fogarty et al. ............ 623/2.38 |
| 8,083,793 B2 * | 12/2011 | Lane et al. ............ 623/2.38 |
| 2001/0021872 A1 | 9/2001 | Bailey et al. |
| 2002/0032481 A1 | 3/2002 | Gabbay |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0212454 A1 | 11/2003 | Scott et al. |
| 2004/0039436 A1 | 2/2004 | Spenser et al. |
| 2004/0186565 A1 | 9/2004 | Schreck |
| 2004/0260389 A1 | 12/2004 | Case et al. |
| 2005/0137682 A1 | 6/2005 | Justino |
| 2005/0137686 A1 * | 6/2005 | Salahieh et al. ............ 623/2.11 |
| 2005/0165479 A1 * | 7/2005 | Drews et al. ............ 623/2.38 |
| 2005/0203614 A1 | 9/2005 | Forster et al. |
| 2005/0203615 A1 * | 9/2005 | Forster et al. ............ 623/2.11 |
| 2005/0203617 A1 | 9/2005 | Forster et al. |
| 2005/0234546 A1 | 10/2005 | Nugent et al. |
| 2006/0025857 A1 | 2/2006 | Bergheim et al. |
| 2006/0149350 A1 | 7/2006 | Patel et al. |
| 2006/0229719 A1 | 10/2006 | Marquez et al. |
| 2006/0235508 A1 * | 10/2006 | Lane et al. ............ 623/2.4 |
| 2006/0259137 A1 | 11/2006 | Artof et al. |
| 2006/0287717 A1 * | 12/2006 | Rowe et al. ............ 623/2.11 |

(56) References Cited

U.S. PATENT DOCUMENTS

| | | | |
|---|---|---|---|
| 2007/0016288 A1* | 1/2007 | Gurskis et al. | 623/2.11 |
| 2007/0203575 A1 | 8/2007 | Forster et al. | |
| 2007/0244546 A1* | 10/2007 | Francis | 623/1.26 |
| 2007/0260305 A1* | 11/2007 | Drews et al. | 623/2.11 |
| 2008/0033543 A1* | 2/2008 | Gurskis et al. | 623/2.11 |
| 2008/0154355 A1 | 6/2008 | Benichou et al. | |
| 2008/0161911 A1 | 7/2008 | Revuelta et al. | |
| 2008/0275550 A1* | 11/2008 | Kheradvar et al. | 623/2.14 |
| 2009/0082857 A1 | 3/2009 | Lashinski et al. | |
| 2009/0132035 A1 | 5/2009 | Roth et al. | |
| 2010/0179648 A1* | 7/2010 | Richter et al. | 623/2.11 |
| 2010/0179649 A1* | 7/2010 | Richter et al. | 623/2.11 |
| 2010/0185275 A1* | 7/2010 | Richter et al. | 623/2.11 |
| 2010/0234940 A1* | 9/2010 | Dolan | 623/2.11 |

FOREIGN PATENT DOCUMENTS

| | | |
|---|---|---|
| DE | 10049814 | 4/2002 |
| EP | 0103546 | 3/1984 |
| EP | 0144167 | 6/1985 |
| EP | 0597967 | 12/1994 |
| EP | 0592410 | 10/1995 |
| EP | 0850607 | 7/1998 |
| EP | 1057460 | 12/2000 |
| EP | 1088529 | 4/2001 |
| EP | 1570809 | 9/2005 |
| EP | 1872743 | 8/2009 |
| FR | 2788217 | 7/2007 |
| GB | 2056023 | 3/1981 |
| WO | WO 91/17720 | 11/1991 |
| WO | WO 92/17118 | 10/1992 |
| WO | WO 93/01768 | 2/1993 |
| WO | WO 97/24080 | 7/1997 |
| WO | WO 98/29057 | 7/1998 |
| WO | WO 99/33414 | 7/1999 |
| WO | WO 99/40964 | 8/1999 |
| WO | WO 99/47075 | 9/1999 |
| WO | WO 00/18333 | 4/2000 |
| WO | WO 00/41652 | 7/2000 |
| WO | WO 00/47139 | 8/2000 |
| WO | WO 01/35878 | 5/2001 |
| WO | WO 01/49213 | 7/2001 |
| WO | WO 01/54624 | 8/2001 |
| WO | WO 01/54625 | 8/2001 |
| WO | WO 01/62189 | 8/2001 |
| WO | WO 01/64137 | 9/2001 |
| WO | WO 01/76510 | 10/2001 |
| WO | WO 02/22054 | 3/2002 |
| WO | WO 02/36048 | 5/2002 |
| WO | WO 02/41789 | 5/2002 |
| WO | WO 02/43620 | 6/2002 |
| WO | WO 02/47575 | 6/2002 |
| WO | WO 02/49540 | 6/2002 |
| WO | WO 03/047468 | 6/2003 |
| WO | WO 2005/087140 | 9/2005 |
| WO | WO 2006/014233 | 2/2006 |
| WO | WO 2006/034008 | 3/2006 |
| WO | WO 2008/005405 | 1/2008 |
| WO | WO 2008/035337 | 3/2008 |
| WO | WO 2008/097589 | 8/2008 |
| WO | WO 2008/147964 | 12/2008 |
| WO | WO 2008/150529 | 12/2008 |

OTHER PUBLICATIONS

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.
Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.
Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.
Serruys, P.W., et al., "Stenting of Coronary Arteries. Are we the Sorcerer's Apprentice?," European Heart Journal (1989) 10, 774-782, pp. 37-45, Jun. 13, 1989.
Kolata, Gina, "Device That Opens Clogged Arteries Gets a Failing Grade in a New Study," nytimes.com, http://www.nytimes.com/1991/01/03/health/device-that-opens-clogged-arteries-gets-a-faili . . . , Jul. 29, 2009, 2 pages.
Urban, M.D., Philip, "Coronary Artery Stenting," Editions Médecine et Hygiène, Genève, 1991, pp. 5-47.
Al-Khaja, N., et al., "Eleven Years' Experience with Carpentier-Edwards Biological Valves in Relation to Survival and Complications," European Journal of Cardiothoracic Surgery 3:305-311, Jun. 30, 2009.
Wheatley, M.D., David J., "Valve Prostheses," Rob & Smith's Operative Surgery, Fourth Edition, pp. 415-424, Butterworths 1986.
Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.
Uchida, Barry T., et al., "Modifications of Gianturco Expandable Wire Stents," AJR:150, May 1988, Dec. 3, 1987, pp. 1185-1187.
Selby, M.D., J. Bayne, "Experience with New Retrieval Forceps for Foreign Body Removal in the Vascular, Urinary, and Biliary Systems," Radiology 1990; 176:535-538.
Inoune, M.D., Kanji, et al., "Clinical Application of Transvenous Mitral Commissurotomy by a New Balloon Catheter," The Journal of Thoracic and Cardiovascular Surgery 87:394-402, 1984.
Al Zaibag, Muayed, et al., "Percutaneous Balloon Valvotomy in Tricuspid Stenosis," British Heart Journal, Jan. 1987, vol. 57, No. 1, pp. 51-53.
Lawrence, Jr., M.D., David D., "Percutaneous Endovascular Graft: Experimental Evaluation," Radiology 1897; 163: 357-360.
Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.
Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.
Rashkind, M.D., William J., "Historical Aspects of Interventional Cardiology: Past, Present, Future," Texas Heart Institute Journal, Interventional Cardiology, pp. 363-367.
Rösch, M.D., Josef, "The Birth, Early Years and Future of Interventional Radiology," J Vasc Interv Radiol 2003; 14:841-853.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Ross, F.R.C.S., D.N., "Aortic Valve Surgery," Guy's Hospital, London, pp. 192-197, approximately 1968.
Rashkind, M.D., William J., "Creationof an Atrial Septal Defect Withoput Thoracotomy," the Journal of the American Medical Association, vol. 196, No. 11, Jun. 13, 1966, pp. 173-174.
Porstmann, W., et al., "Der Verschluβ des Ductus Arteriosus Persistens ohne Thorakotomie," Thoraxchirurgie Vaskuläre Chirurgie, Band 15, Heft 2, Stuttgart, im Apr. 1967, pp. 199-203.
Curriculum Vitae of Robert A. Ersek, M.D., FACS, Jul. 10, 2009, http://www.ersek.com/rae-cv.htm.
International Search Report for Corresponding PCT Case No. PCT/US2011/027351 dated Nov. 28, 2011.

* cited by examiner

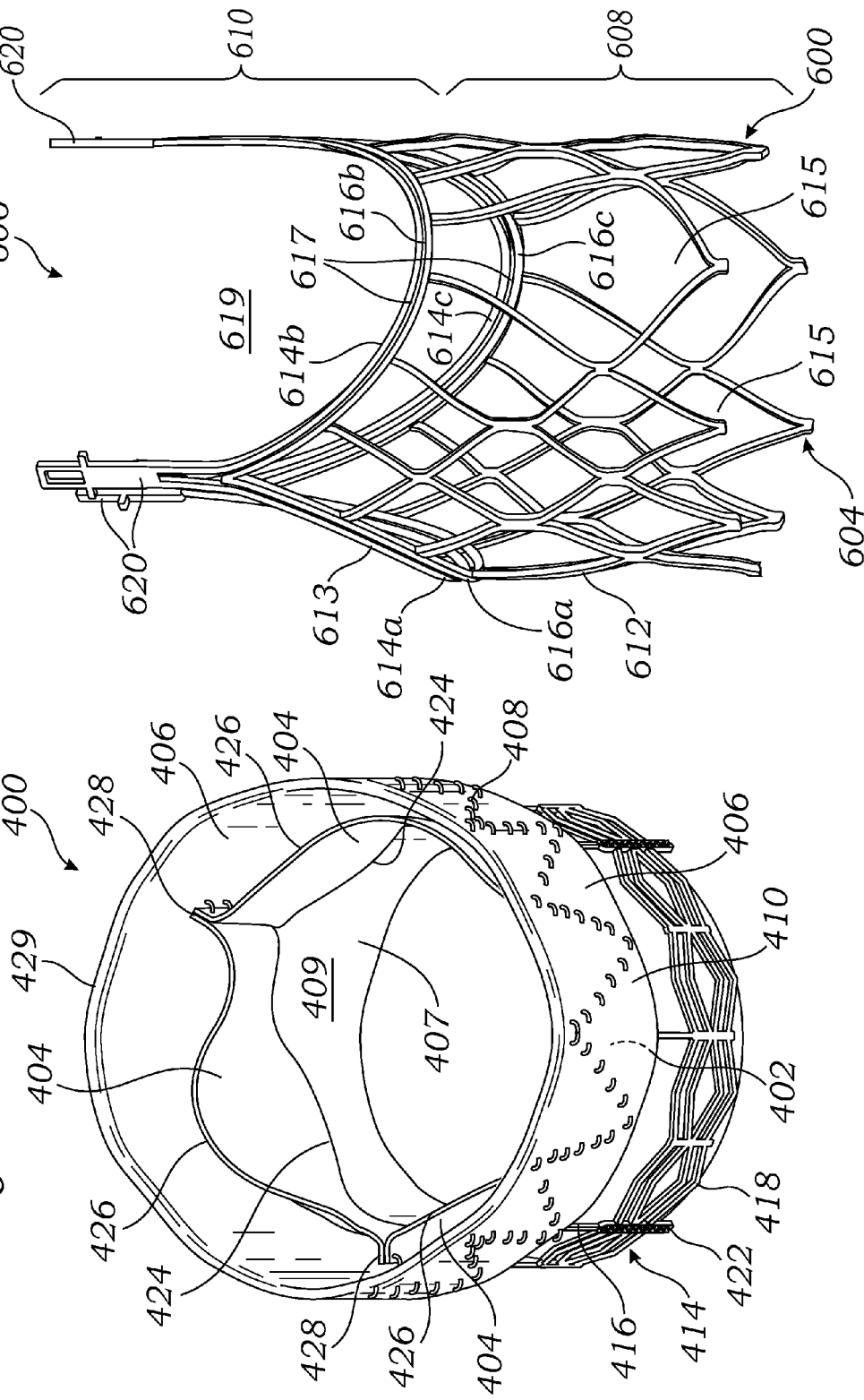

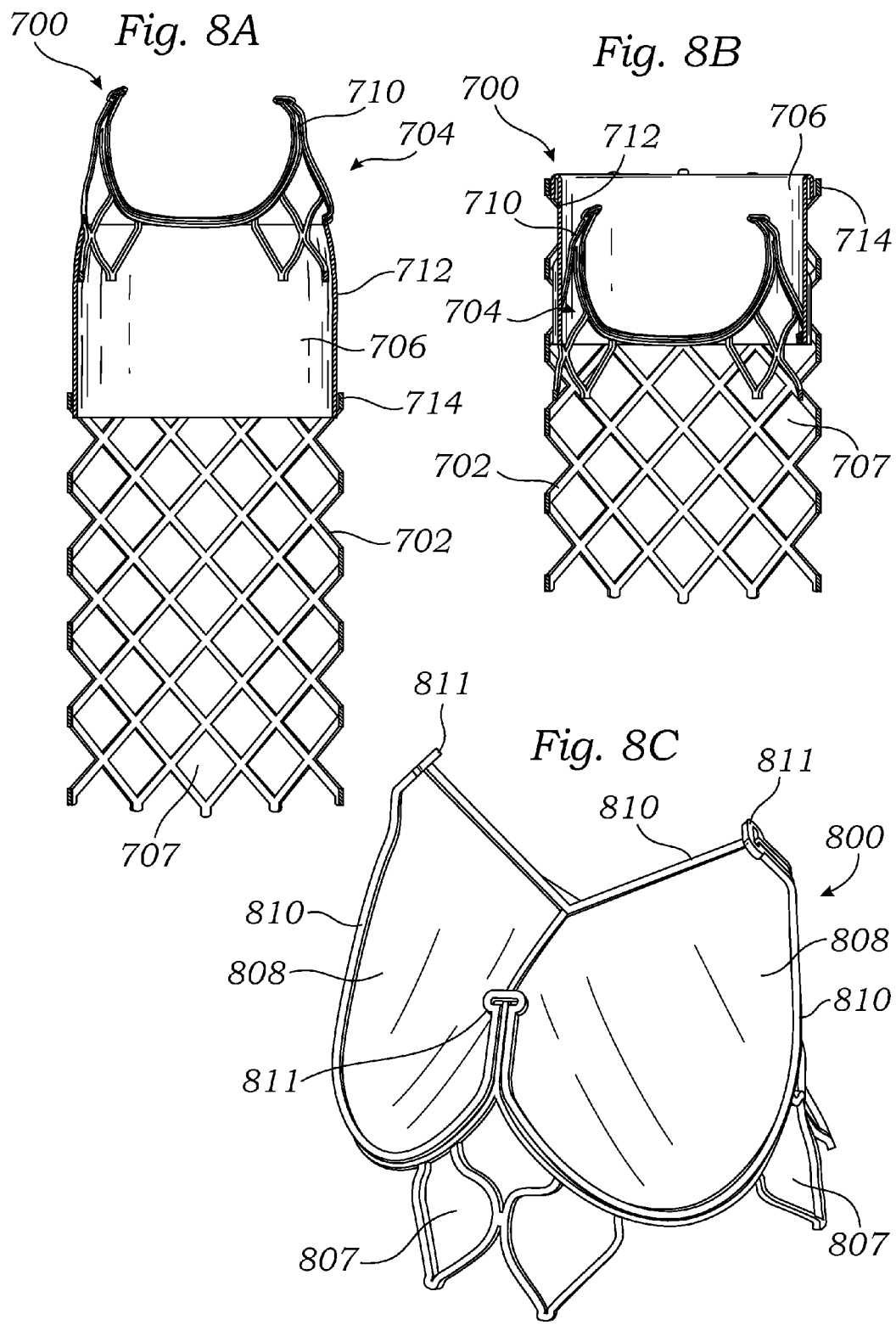

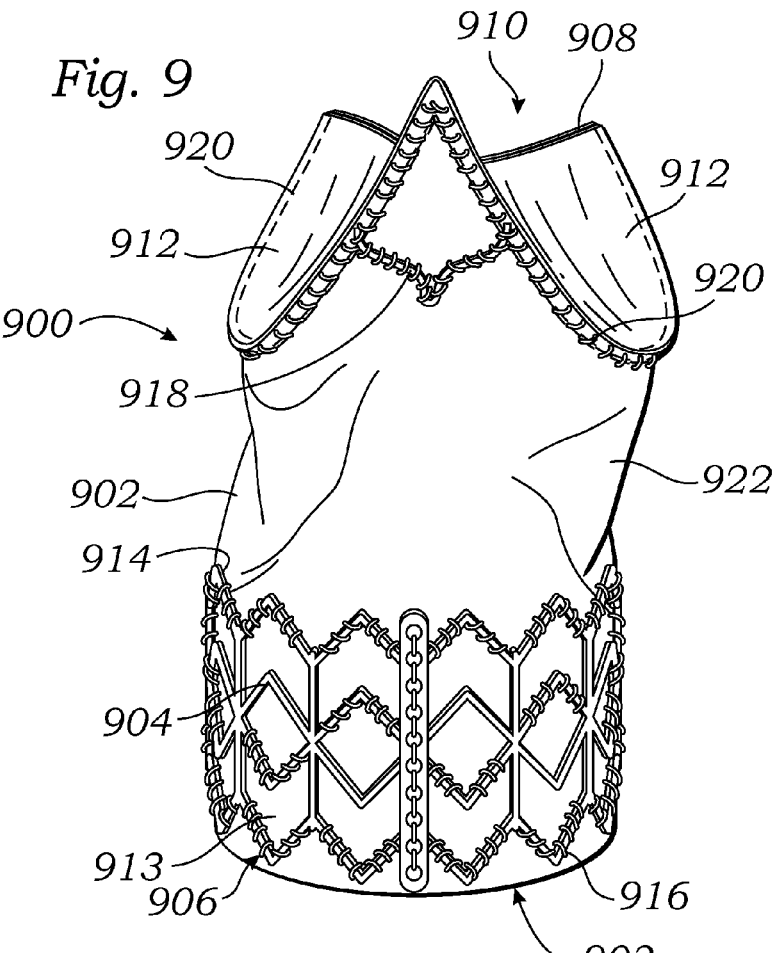
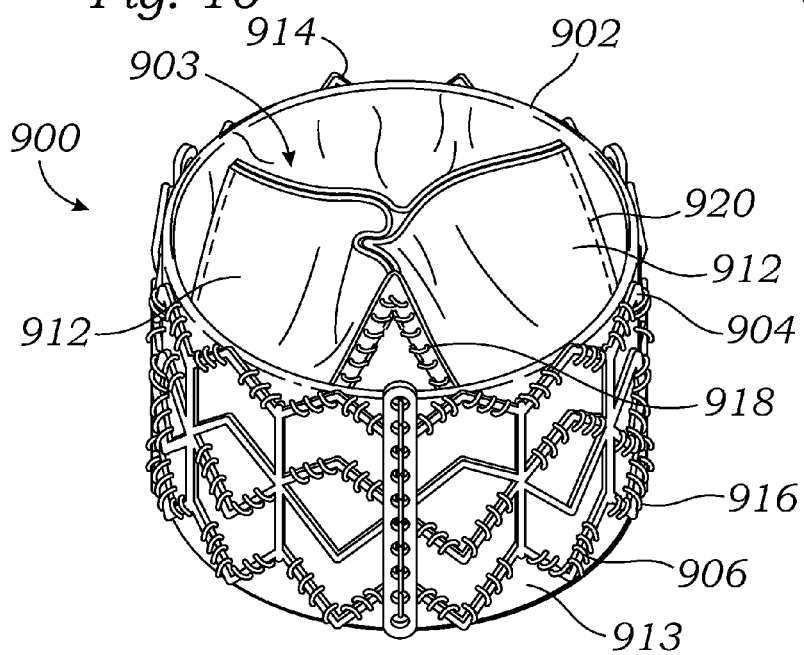

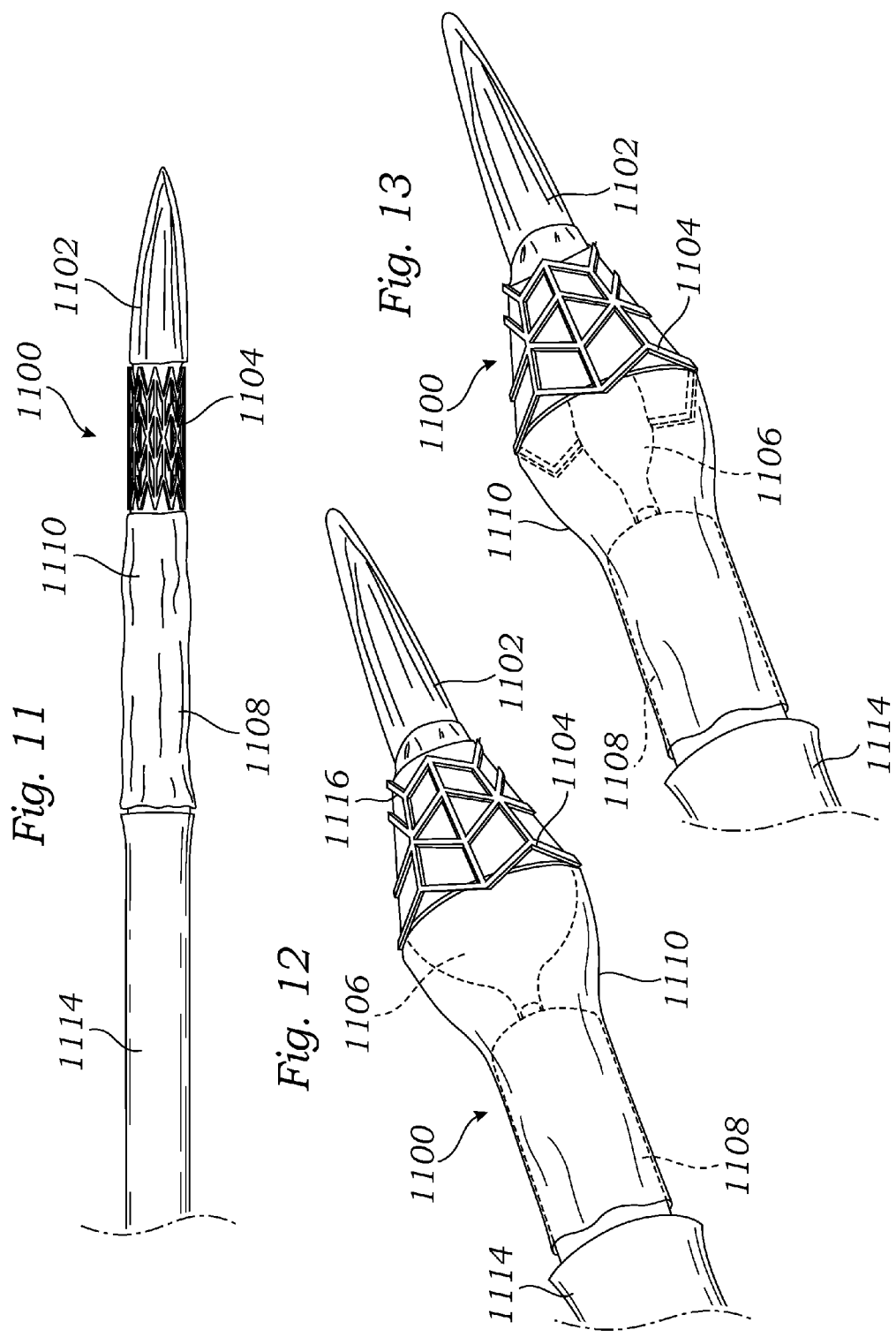

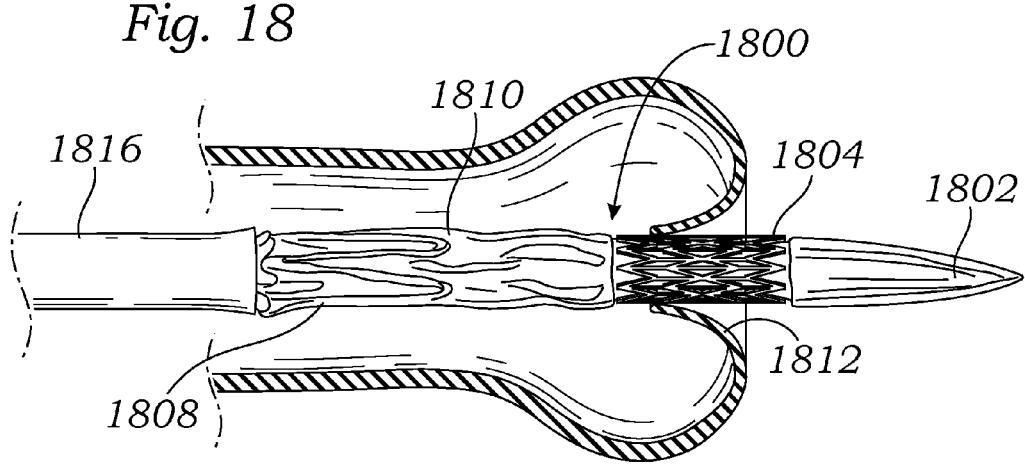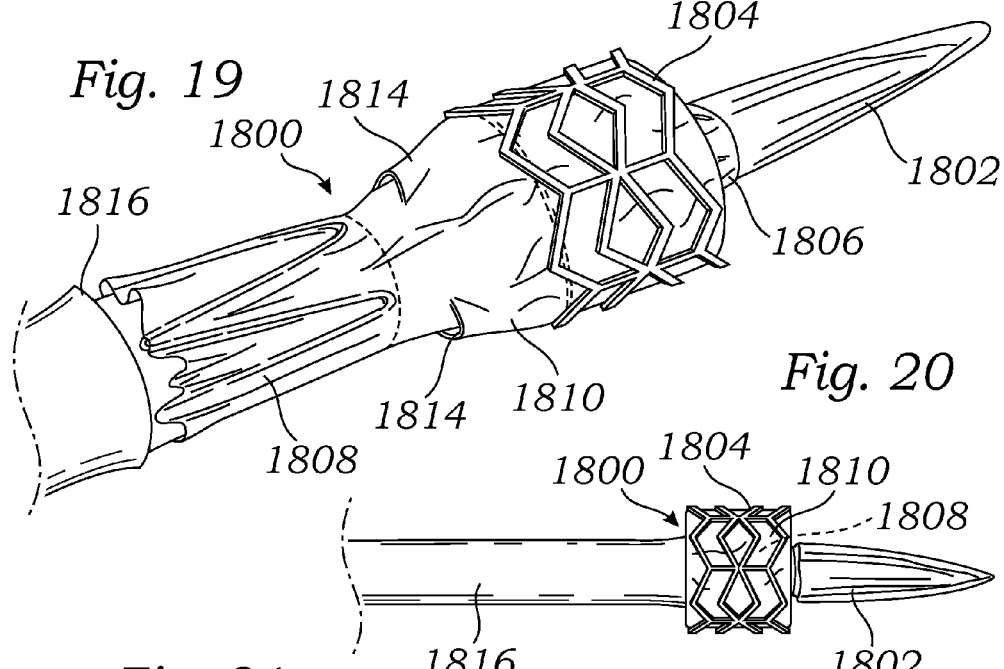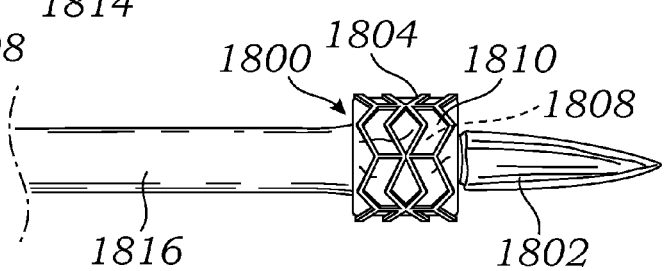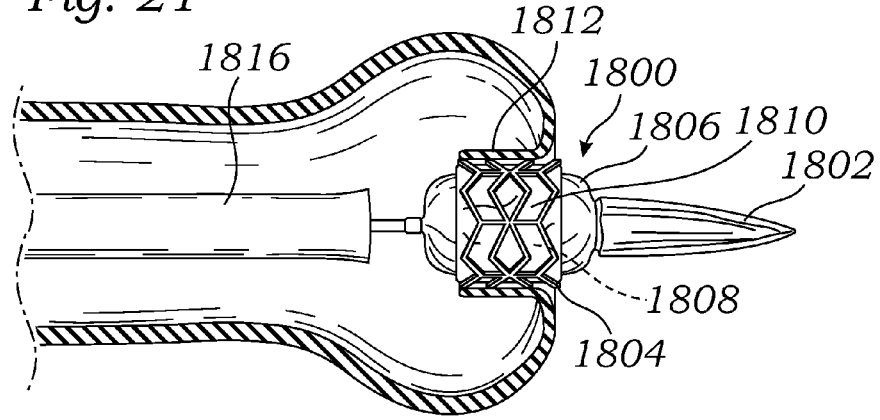

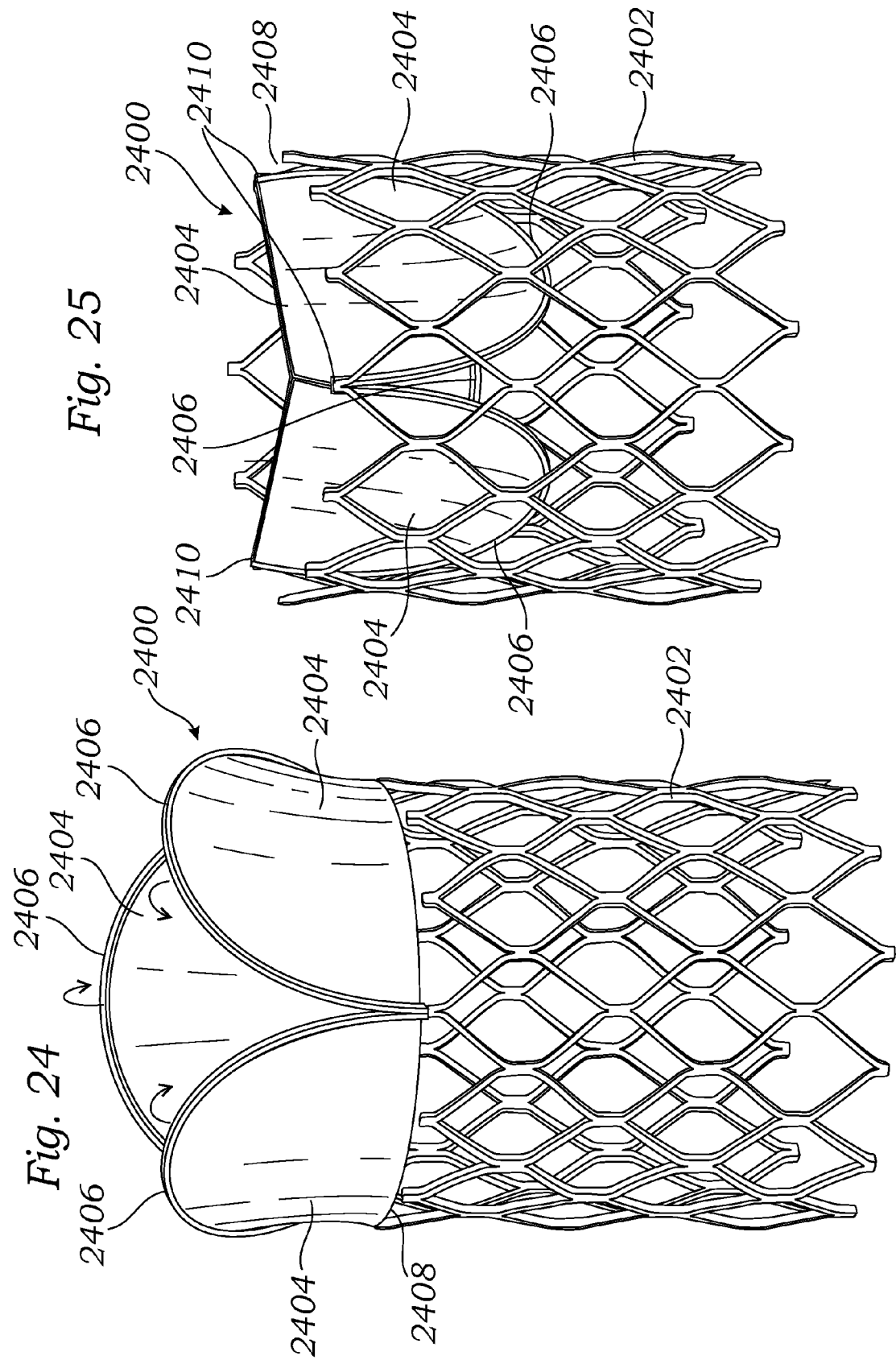

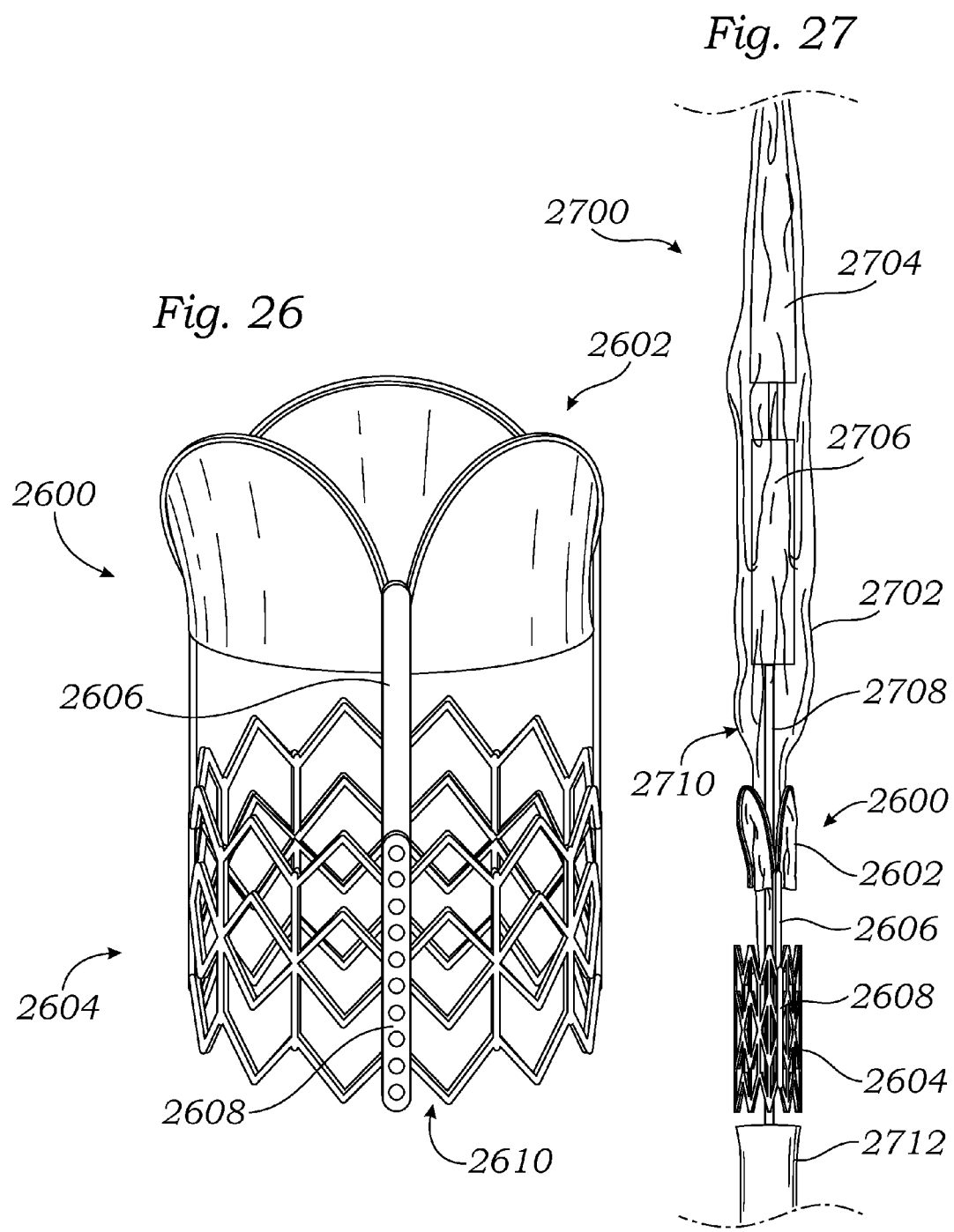

LOW-PROFILE HEART VALVE AND DELIVERY SYSTEM

FIELD

The present invention relates to implantable devices. More particularly, the present invention relates to devices and methods for implantation of a prosthetic heart valve.

BACKGROUND

A transcatheter heart valve (THV) is a prosthetic, or replacement, heart valve which is configured to be implanted by a catheterization technique. One type of THV has been developed by Edwards Lifesciences of Irvine, Calif. and is described in U.S. Pat. No. 6,730,118, which is hereby incorporated by reference in its entirety. The THV described in the '118 patent is primarily configured for replacing the function of a stenotic aortic valve in a human heart. An important feature of the THV is the ability to be implanted within the stenotic region of the native aortic valve. After implantation, the THV holds open the leaflets of the native aortic valve and utilizes the native valve annulus as an attachment means for the THV.

Such transcatheter techniques traditionally involve the implantation of a prosthetic valve that can be compressed or folded to a reduced diameter. By compressing or folding the prosthetic valve to a reduced diameter, the prosthetic valve can be delivered through a less invasive penetration to a desired target location within the human anatomy. Thereafter, the compressed valve is traditionally released, expanded, separated from the delivery system, and secured to the desired target location.

An important design parameter of the THV is the diameter of its folded or crimped profile. The diameter of the crimped profile is important because it directly influences the physician's ability to advance the THV through the femoral artery or vein. More particularly, a smaller profile allows for treatment of a wider population of patients, with enhanced safety.

U.S. Pat. No. 7,381,219 (the '219 Patent) discloses a replacement heart valve having a replacement valve collapsed within the lumen of an anchor. Col. 7, lines 35-36. "Retraction of wires 50 relative to tubes 60 foreshortens anchor 30, which increases the anchor's width while decreasing its length." Col. 7, lines 36-38. The '219 patent also discloses a two-piece apparatus comprising an expandable anchor piece and an expandable replacement valve piece. The anchor piece includes a groove section that is "adapted to engage an expandable frame portion" of the valve piece, in order to couple the anchor piece to the valve piece. Col. 17, lines 38-41. Such coupling can be complicated to perform and can make implantation difficult.

European Patent EP 1 872 743 discloses a cardiovascular valve assembly comprising a replaceable valve member and an expandable base member designed to account for patient growth. "After installation of base member 100, tubular body 110 may be dilated to a small diameter during a first procedure. A valve member 20 having a small diameter frame 30 can be docked with base member 100 by insertion of fingers 50 into opening 154." Col. 7, line 57 to col. 8, line 4. Again, this method of inserting fingers into openings in the disclosed design can be complicated to perform.

International Application No. PCT/US2008/001590 discloses a valve having "a valve leaflet 104 that] can be coupled adjacent to the proximal end 112 of the valve frame 102 at junction points 120." Page 4. A "leaflet transition member 110 [is] coupled to at least a portion of the valve leaflet 104 and/or the leaflet frame 111. Page 4. "Elongate push members" on a delivery catheter "can be used to push the leaflet transition member 310 inside the lumen 308 of the valve 300." Page 10.

These replacement heart valves can be complicated to manufacture and/or implant within a patient's body. A need thus remains for an improved replacement heart valve that can address these and other disadvantages associated with conventional replacement heart valves.

SUMMARY

Traditionally, replacement valves, such as replacement heart valves (e.g., the THV) are crimped directly onto a balloon of a balloon catheter and the crimped replacement valve and balloon are navigated through the patient's vasculature to the implantation site. Because of the thickness of the balloon material, the valve cannot be crimped to its smallest possible profile. In certain embodiments disclosed below, at least a portion of the disclosed replacement valves can be crimped on to a delivery catheter at a location separate from the balloon and/or the valve portion and stent or anchor portion of the replacement valve can be axially separated from one another when crimped on the delivery catheter. This allows some embodiments of the disclosed replacement valves to be crimped to a smaller diameter than conventional replacement heart valves. After the THV is advanced through narrow portions in a patient's vasculature (for example, the iliac artery), some embodiments of the disclosed replacement valves can be transitioned from the delivery configuration to an operating configuration. Such transitioning, or transformation, can be completed before or after positioning the replacement valve within the native valve annulus.

Generally, disclosed replacement valves are adapted to be radially collapsed or compressed (e.g., crimped) to facilitate navigation through the narrow passages of a patient's vasculature to the treatment site within the patient's body. After the replacement valve reaches the treatment site (e.g., the aortic valve annulus) and/or has traveled through the narrowest parts of the patient's vasculature, the replacement valve can be radially expanded within the native valve annulus. At some point during delivery of disclosed replacement valves, the valve can be expanded and/or transitioned from a delivery configuration, which can minimize the crimped profile, to an operating configuration. In some embodiments, the replacement valve is expanded such that at least a portion of the replacement valve has a diameter sufficient to engage the native valve annulus. In some embodiments, the replacement valve can both be expanded and transitioned to an operating configuration, as will be explained in further detail below.

Certain embodiments of a prosthetic valve (e.g., a replacement heart valve) comprise a stent portion (e.g., a generally tubular stent portion) defining a lumen through said stent portion, a valve portion comprising one or more leaflets, and a flexible sleeve configured to couple the valve portion to the stent portion. The prosthetic valve can be transformable from a delivery configuration, in which at least a portion of the one or more leaflets is positioned outside the lumen of the stent portion, to an operating configuration, in which at least a portion of the one or more leaflets is positioned within the lumen of the stent portion.

In some embodiments of a prosthetic valve, the stent portion is coupled to the valve portion by a flexible sleeve. A lower portion of the flexible sleeve can be positioned within the lumen of the stent portion, and the flexible sleeve can extend from the lower portion to an upper portion, wherein the upper portion of the flexible sleeve is positioned adjacent an exterior surface of the valve portion. In some embodiments, the valve portion can be configured to be pushed or pulled into the lumen of the stent portion, resulting in the flexible sleeve being positioned between an outer surface of the valve portion and an inner surface of the stent portion once the prosthetic valve is transformed or transitioned to the operating configuration.

In particular embodiments, the one or more leaflets can each comprise a free end and a secured end. Each of the secured ends of the leaflets can be coupled to the flexible sleeve, and each of the free ends of the leaflets can be freely moveable apart from the flexible sleeve. In some embodiments, while the replacement valve is in the delivery configuration, the one or more leaflets can be arranged such that each of the secured ends is positioned above each of the free ends, and while the replacement valve is in the operating configuration, the one or more leaflets can be arranged such that each of the secured ends is positioned below each of the free ends. Thus, the leaflets can be inverted during the process of transitioning from the delivery configuration to the operating configuration.

In some embodiments of a replacement valve comprising a flexible sleeve, the flexible sleeve can be flipped inside out (e.g., inverted) during transitioning between the delivery configuration and the operating configuration. For example, the flexible sleeve can comprise an inner surface facing the lumen of the stent portion and an outer surface to which the one or more leaflets are coupled while in the delivery configuration. The stent portion can comprise a lumen surface defining the lumen of the stent portion and an external surface, and the inner surface of the flexible sleeve can be coupled to the external surface of the stent portion. In the operating configuration, at least a portion of the outer surface of the flexible sleeve can be positioned within and facing the lumen of the stent portion. Thus, the flexible sleeve can be flipped inside out (or outside in).

Certain embodiments can include a temporary valve. The valve portion can be coupled to a first end of the stent portion, and the temporary valve can be coupled to a second end of the stent portion, opposite the first end of the stent portion. Such temporary valves can function as an interim replacement heart valve while the main replacement valve is being positioned and/or transitioned to the operating configuration. Once the main replacement valve has been fully implanted and deployed, the temporary valve can be removed, such as by being removed along with the delivery system, in some embodiments. Alternatively, the temporary valve can be resorbable or can simply remain in the native valve, coupled to the main replacement valve. For example, in some embodiments, the flexible sleeve can include at least one slit through which blood can flow at least when the valve is in the delivery configuration. The slits can thus function as a temporary valve in some embodiments. In these embodiments, the temporary valve is not removed after it is no longer necessary (e.g., after the valve portion of the replacement valve is fully deployed and operating).

The valve portion can be coupled to the stent portion of the replacement valve in a variety of ways. For example, in some embodiments, the stent portion can be coupled to the valve portion by a longitudinal sliding rail. In some embodiments, the stent portion can be coupled to the valve portion by one or more hinges configured to allow the one or more leaflets to be inverted from a first position outside the lumen of the stent portion to a second position within the lumen of the stent portion. In other embodiments, the valve portion can be coupled to the stent portion of the replacement valve by, for example, connecting members, extensions of the stent portion, and/or a flexible sleeve or skirt.

One embodiment of a prosthetic valve can comprise a radially collapsible and expandable frame and a leaflet structure. The leaflet structure can comprise a plurality of leaflets, a plurality of reinforcement elements, and a plurality of leaflet-supporting members. The frame can be coupled to the leaflet structure, such that the leaflets are positioned at least substantially outside of the frame, wherein a portion of each of the leaflets is positioned in a respective gap formed between a respective reinforcement element and a respective leaflet-supporting member.

In some embodiments, the frame can be coupled to the leaflet structure by a plurality of connecting members. For example, the frame and the connecting members can each comprise a plurality of open cells. The frame can comprise open cells substantially around its entire circumference, while the connecting members can comprise a few open cells extending from the frame to the leaflet structure. In some embodiments, each of the leaflet-supporting members of the leaflet structure can be positioned to be a boundary for the plurality of open cells. Thus, in some embodiments, no open cells extend into the windows defined by the reinforcement arcs, and thus there are no open cells external to the leaflets in some embodiments (e.g., none of the open cells are positioned between the leaflets and the native valve annulus).

Some embodiments of a prosthetic valve can include a flexible sleeve positioned adjacent at least a portion of the frame. In some embodiments, the flexible sleeve can be configured to couple the leaflet structure to the frame.

In certain embodiments, at least a portion of each of the leaflet-supporting members can be separated from the frame along the axial direction. For example, certain portions of the leaflet structure can be coupled to certain portions of the frame, such as by connecting members, while other portions of the leaflet structure can be free from the frame (e.g., in areas without connecting members, there can exist a gap along the axial direction between the leaflet structure and the frame). In some embodiments, the prosthetic valve can be configured to be transformable from a delivery configuration in which each of the leaflet-supporting members is separated from the frame along the axial direction, to an operating configuration in which a least a portion of each of the leaflet-supporting members is positioned within a lumen of the frame Some embodiments of a prosthetic valve can be configured such that the leaflet structure is positioned supraannularly to a native valve annulus. For example, in some embodiments, the frame can be positioned within the native valve annulus, while the leaflet structure is positioned supraannularly (e.g., above the native valve annulus).

Particular embodiments can be configured such that the reinforcement elements are arranged to form a duckbill shape, with each pair of adjacent reinforcement elements joined to one another at a commissure point.

In some embodiments, the frame can be coupled to the leaflet structure by at least one sliding rail.

In some embodiments, the frame can be configured to expand to an expanded diameter sufficient to engage a native valve annulus, thereby anchoring the prosthetic valve, and the leaflet structure can be configured to expand to a second diameter less than the expanded diameter, so as to not contact the native valve. In some embodiments, the frame does not overlap the leaflet structure.

Methods of implanting replacement heart valves are also disclosed. In some such methods, the replacement heart valve can comprise a stent portion, a valve portion, and a flexible sleeve coupled to the stent portion. The stent portion can comprise an outer surface and an inner surface defining a lumen, and the valve portion can comprise a plurality of leaflets. While the replacement valve is in the delivery configuration, at least a portion of the leaflets can be positioned outside of the lumen defined by the stent portion. In some methods, the replacement heart valve can be mounted onto a delivery system in a delivery configuration, advanced to an implant position adjacent a heart valve annulus, transitioned from the delivery configuration to an operating configuration, and radially expanded so as to anchor it within the heart valve annulus. For example, the replacement heart valve can be expanded such that the stent portion engages the heart valve annulus, thereby anchoring the replacement heart valve in position within the heart valve annulus. In some methods, while the replacement valve is in the operating configuration at least a portion of the leaflets can be positioned within the lumen defined by the stent portion.

In some methods, the delivery system is removed from the replacement heart valve. Transitioning the replacement valve from the delivery configuration to the operating configuration can occur prior to removing the delivery system from the replacement heart valve.

In some methods, a lower end of the flexible sleeve can be coupled to the stent portion, and transitioning the replacement valve from the delivery configuration to the operating configuration can comprise inverting the flexible sleeve such that an upper end of the flexible sleeve opposite the lower end of the flexible sleeve is moved to a position within the lumen of the stent portion. In some embodiments, the flexible sleeve can be folded onto itself as the valve portion is positioned within the lumen of the stent portion. The flexible sleeve can comprise a plurality of slits arranged to function as a temporary valve during implanting of the replacement valve.

In certain methods, a lower end of the flexible sleeve can be coupled to the inner surface of the stent portion, and transitioning the replacement valve from the delivery configuration to the operating configuration can comprise folding the flexible sleeve onto itself as the valve portion is positioned within the lumen of the stent portion.

In some methods, transitioning the replacement valve from the delivery configuration to the operating configuration can comprise partially expanding the stent portion into a tapered configuration and positioning the valve portion at least partially within the lumen of the stent portion. Radially expanding the replacement heart valve can comprise expanding fully the valve portion and the stent portion together.

Various steps of the disclosed methods can generally be performed in different orders. For example, advancing the replacement heart valve to an implant position can occur after positioning the valve portion at least partially within the lumen of the stent portion in some embodiments. Alternatively, advancing the replacement heart valve to an implant position can occur before positioning the valve portion at least partially within the lumen of the stent portion.

In embodiments of methods that include transitioning the replacement valve from a delivery configuration to an operating configuration, disclosed methods can employ any suitable technique for transitioning the replacement valve. For example, transitioning the replacement valve from the delivery configuration to the operating configuration can comprise sliding the valve portion along a sliding rail into position within the lumen of the stent portion. In some embodiments, transitioning the replacement valve from the delivery configuration to the operating configuration can comprise inverting the plurality of leaflets from a first position outside of the lumen of the stent portion to a second position within the lumen of the stent portion.

The present disclosure also concerns embodiments of a prosthetic heart valve system. Such embodiments can include a delivery apparatus comprising an expansion device and a delivery catheter on which the expansion device is mounted and a radially-expandable replacement valve mounted in a radially compressed state on the delivery catheter. The replacement valve can comprise a valve portion and a stent portion separated from one another along an axial direction and coupled by at least one pair of sliding rails. The expansion device can be configured to expand the replacement valve and to position at least part of the valve portion within a lumen of the stent portion by moving valve portion along the at least one pair of sliding rails.

The foregoing and other objects, features, and advantages of the invention will become more apparent from the following detailed description, which proceeds with reference to the accompanying figures.

BRIEF DESCRIPTION OF THE DRAWINGS

FIG. 5 is a perspective view of the replacement heart valve shown in FIG. 4, in an operating configuration.

FIG. 6 shows a perspective view of the frame of another embodiment of a replacement heart valve.

FIG. 8A is a section view of the replacement heart valve of FIG. 7, shown in a delivery configuration.

FIG. 8B is a section view of the replacement heart valve of FIG. 7, shown in an operating configuration.

FIG. 8C is a perspective view of the valve portion of one embodiment of a replacement heart valve.

FIG. 9 is a perspective view of one embodiment of a replacement heart valve according to the present disclosure, in a delivery configuration.

FIG. 10 is a perspective view of the replacement heart valve of FIG. 9, after being transitioned to an operating configuration.

FIG. 11 shows an elevation view of a replacement heart valve crimped onto a delivery catheter.

FIG. 12 is a perspective view of a replacement valve being partially expanded while on a delivery catheter.

FIG. 13 is a perspective view showing deflation of the balloon used to expand the stent portion of a replacement heart valve according to one disclosed method.

FIG. 18 shows an elevation view of a replacement heart valve crimped onto a delivery catheter being positioned within a patient's native valve, according to one disclosed method.

FIG. 19 is a perspective view of the stent portion of a replacement valve being expanded, while the valve portion of the replacement valve remains crimped onto the delivery catheter.

FIG. 20 is an elevation view of the replacement valve shown in FIGS. 18-19, with the valve portion being pushed into the stent portion of the replacement heart valve.

FIG. 21 is an elevation view of the replacement heart valve being fully expanded to an operating configuration within a patient's native valve annulus.

FIG. 24 is a perspective view of one embodiment of a replacement heart valve having moveable leaflets, shown in a delivery configuration.

FIG. 25 is a perspective view of the replacement heart valve of FIG. 24, with the leaflets shown in an operating configuration.

FIG. 26 is a perspective view of a two-part replacement heart valve.

FIG. 27 is an elevation view of a two-part replacement heart valve crimped onto a delivery system.

DETAILED DESCRIPTION

Figure 1:
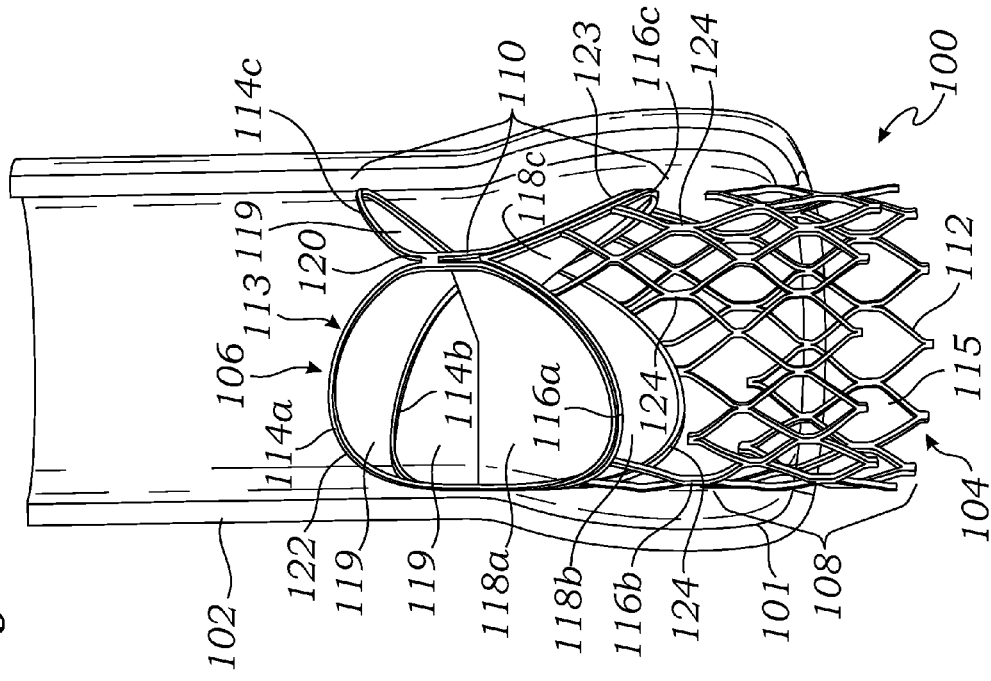
FIG. 1 is a perspective view of one embodiment of a replacement heart valve according to the present disclosure.

As used in this application and in the claims, the singular forms "a," "an," and "the" include the plural forms unless the context clearly dictates otherwise. Additionally, the term "includes" means "comprises." Further, the terms "coupled" generally means electrically, electromagnetically, and/or physically (e.g., mechanically or chemically) coupled or linked and does not exclude the presence of intermediate elements between the coupled items.

As used herein, the "expanded" or "deployed" state of a valve assembly or frame refers to the state of the valve assembly/frame when radially expanded to its functional size. The "crimped", "compressed" or "folded" state of a valve assembly or frame refers to the state of the valve assembly/frame when radially compressed or collapsed to a diameter suitable for delivering the valve assembly through a patient's vasculature on a catheter or equivalent mechanism. "Partially crimped" or "partially compressed" or "partially expanded" means that at least a portion of a valve assembly/frame has a diameter that is less than the diameter of the valve assembly/frame in the expanded state and greater than the diameter of the valve assembly/frame in the compressed state.

The terms "delivery configuration" and "operating configuration" refer to the arrangement of the components of the replacement valve relative to one another, and each term includes both crimped and non-crimped (e.g., expanded) states. The term "fully assembled" refers to replacement valves in which all required components are coupled together, and thus a replacement valve can be considered fully assembled in both delivery and operating configurations, even when in a crimped position on a delivery catheter.

Terms such as "above," "upper," "below," and "lower" are meant only to show the position of some features relative to others as shown in the drawings, and do not necessarily correlate to actual positions or directions of those features when the replacement valve is being delivered and/or is in its implanted configuration or position.

Descriptions and disclosures provided in association with one particular embodiment are not limited to that embodiment, and may be applied to any embodiment disclosed.

Moreover, for the sake of simplicity, the figures may not show the various ways (readily discernable, based on this disclosure, by one of ordinary skill in the art) in which the disclosed system, method, and apparatus can be used in combination with other systems, methods, and apparatuses.

Disclosed embodiments of a replacement heart valve can be designed for delivery and implantation using minimally invasive techniques. For example, disclosed replacement heart valves can be crimped onto a delivery catheter, navigated through a patient's vasculature, and expanded before or during implantation in a native valve site, such as the native aortic valve. As such, the minimum crimped diameter (e.g., the profile of the crimped replacement valve on the delivery system) can be of utmost importance to the success and/or ease of performing of the procedure.

The minimum crimped diameter is dictated at least in part by the amount of material that the valve contains in its radial direction. Prior art valves sought to create a reduced crimped diameter by either separating components of the valve axially, which created a relatively long apparatus, or assembling the valve after crossing the narrowest portion of the vasculature (e.g., the arc of the femoral artery). Embodiments of the presently disclosed heart valves can be fully assembled prior to insertion into a patient. For example, in some embodiments different components of a replacement heart valve need not be coupled together during delivery, but rather, the components are just moved relative to one another while remaining coupled together. In some embodiments, portions of the replacement valve are not separable from one another without damage to (e.g., destruction of) the replacement valve.

Figure 2:
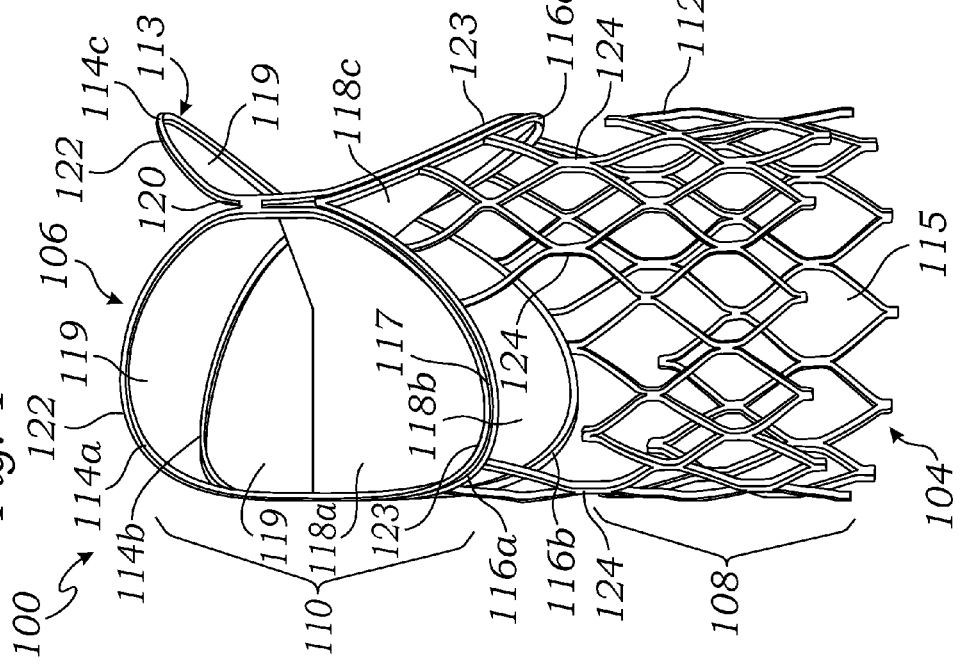
FIG. 2 is a perspective view of the replacement valve of FIG. 1, shown implanted in a patient's aortic valve.
Figure 3:
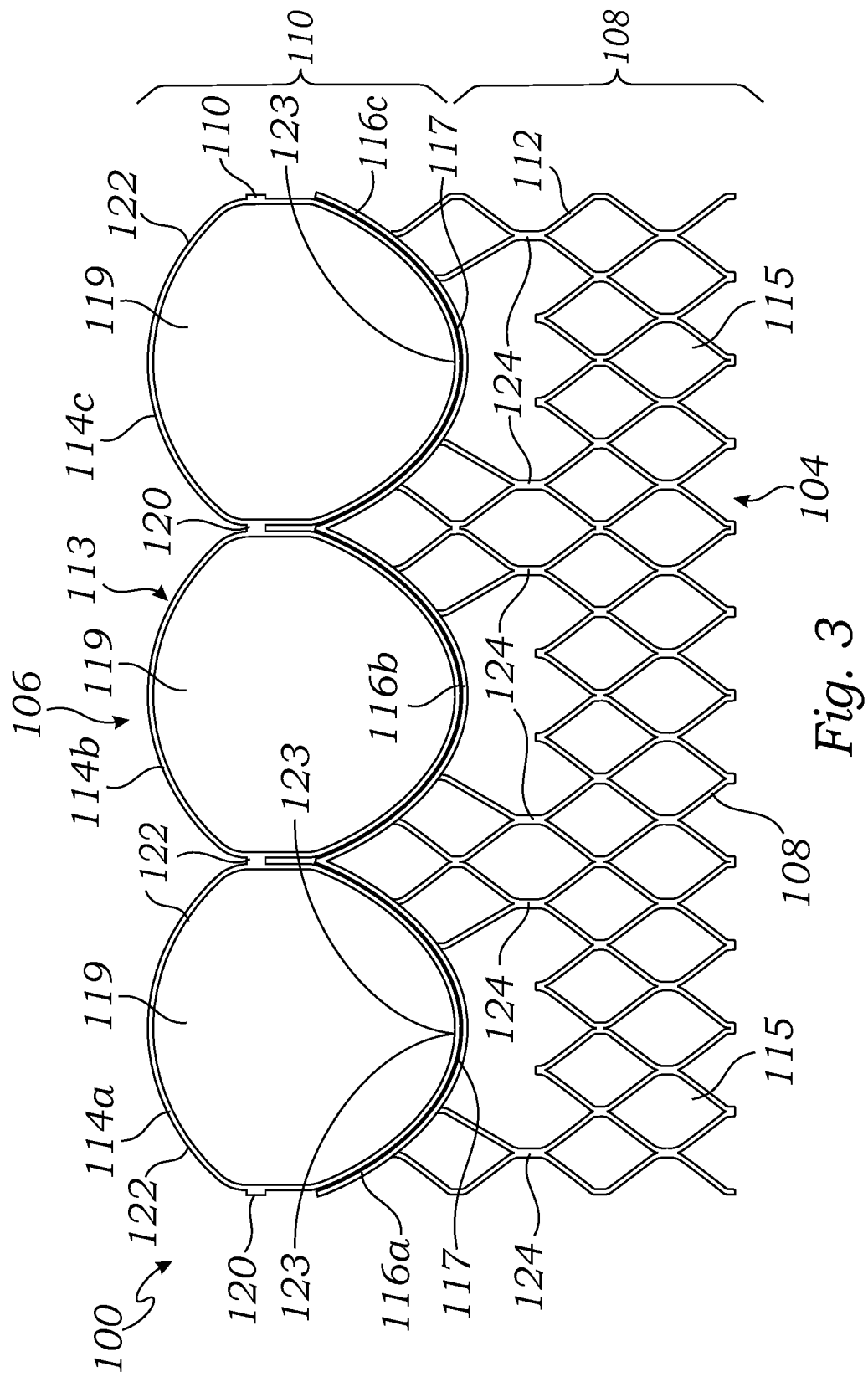
FIG. 3 is an elevation view of the frames of the replacement valves shown in FIGS. 1-2, cut open and laid flat.

FIGS. 1-3 illustrate one embodiment of a replacement heart valve 100 that can be deployed, for example, at least partially in a patient's aorta 102. As shown in FIG. 2, replacement heart valve 100 can be implanted such that the leaflets are positioned supraannularly within the aorta 102, while a portion of the replacement valve is positioned within the native valve annulus. FIG. 3 shows a flattened view of the replacement valve 100 shown in FIGS. 1-2 (e.g., FIG. 3 shows replacement valve 100 cut open and laid flat).

As with all disclosed embodiments, replacement valve 100 can be configured to be radially collapsible to a collapsed or crimped state for introduction into the body on a delivery catheter and radially expandable to an expanded state for implanting the valve at a desired location in the body (e.g., the native aortic valve). At least part of the replacement valve 100 can be made of a plastically-expandable material (e.g., stainless steel, chromium alloys, and/or other suitable materials) that permits crimping of the valve to a smaller profile for delivery and expansion of the valve using an expansion device such as the balloon of a balloon catheter. Alternatively or additionally, at least part of the replacement valve 100 can be a so-called self-expanding valve made of a self-expanding material such as Nitinol. For example, a self-expanding valve can include a self-expanding lower portion (e.g., a self-expanding frame or stent) and/or a self-expanding leaflet support frame. A self-expanding valve can be crimped to a smaller profile and held in the crimped state with a restraining device such as a sheath covering the valve. When the valve is positioned at or near the target site, the restraining device can be removed to allow the valve to self-expand to its expanded, functional size.

Replacement valve 100 comprises an inflow end 104 and an outflow end 106. When in place within a patient's heart, blood flows into the valve 100 at the inflow end 104 and out of the valve 100 at the outflow end 106. Replacement valve 100 generally includes a lower portion 108 adjacent the inflow end 104 and a leaflet portion 110 adjacent the outflow end 106. Lower portion 108 can serve to keep the native valve open and can be positioned within the native valve annulus 101. Lower portion 108 can also help to fix or anchor the replacement valve 100 in place with the patient's native valve (e.g., the lower portion 108 can be positioned to be in contact with the aortic annulus and the native valve). Lower portion 108 can also serve as a basis for anchoring the leaflet portion 110, while the leaflet portion 110 can be positioned supraannularly (e.g., above the native valve annulus 101) and need not contact the aortic wall, but can contact the aortic wall in some embodiments. For example, in some embodiments, a gap can exist between the leaflet potion 110 and the aortic wall (e.g., at least a part of the leaflet portion 110 does not contact the vessel wall in some embodiments). In some embodiments, the replacement valve 100 can be positioned and sized relative to the patient's aorta such that a gap exists between the replacement valve 100 and the aortic wall and/or aortic sinuses. In this manner, blood can flow between the aortic wall and the leaflet portion 110 (e.g., when the leaflets are closed, during diastole), thereby supplying blood to the coronary arteries. Thus, the lower portion 108 can anchor the replacement valve 100 in place against the native valve, while the leaflet portion 110 is not anchored to the native valve or vessel in some embodiments. The valve can have a sealing member 126 (FIG. 28) on the outside of the stent structure 112 to block the back flow of blood into the stent structure, through the aortic annulus, and into the left ventricle during diastole.

Lower portion 108 includes a stent structure, or anchor portion, 112 (e.g., a wire mesh frame). The stent structure can comprise, for example, one or more rows of open cells 115, arranged circumferentially. The leaflet portion 110 can include a leaflet support frame 113 that comprises reinforcement elements 114a, 114b, 114c and leaflet-supporting members 116a, 116b, 116c. The leaflet support frame 113 can be a two-part scalloped frame in some embodiments. In other embodiments, the leaflet support frame 113 can comprise a single integral body.

Reinforcement elements 114a, 114b, 114c comprise respective upper arcs 122 connected to respective lower arcs 123 so as to define respective windows, or openings 119. Respective reinforcement elements 114a, 114b, 114c can be arranged with respect to one another so as to form a duckbill shape as shown in FIG. 1, and can be connected to each other by commissure posts 120. Such an arrangement can substantially prevent injury to the native tissue in some embodiments.

Lower arcs 123 of the reinforcement elements 114a, 114b, 114c can be positioned with respect to leaflet-supporting members 116a, 116b, 116b so as to define a gap 117a, 117b, 117c therebetween. Leaflets 118a, 118b, 118c can be secured in the gap 117a, 117b, 117c between a respective reinforcement element 114a, 114b, 114c and leaflet-supporting member 116a, 116b, 116c. For example, leaflet 118a can be secured in place in the gap 117a defined by reinforcement element 114a and leaflet-supporting member 116a.

A lower edge portion of each of the leaflets 118a, 118b, 118c can be sandwiched between the reinforcement elements and leaflet-supporting members, as shown in FIGS. 1 and 2 such that the leaflets 118a, 118b, 118c can operate (e.g., open and close) within windows 119 defined by the reinforcement elements 114a, 114b, 114c. Some suitable attachment methods are described in United States Patent Application Publication No. 2009/0157175 (the '175 Publication), which is hereby incorporated herein by reference in its entirety. For example, in one specific embodiment described in the '175 Publication, the leaflets 118 can be secured (e.g., sutured) to a cloth which can substantially wrap around reinforcement elements 114 and leaflet-supporting members 116. Portions of the cloth can be secured (e.g., sutured) together, thereby effectively securing the reinforcement elements 114 to the leaflet-supporting members 116.

Some configurations can allow for the leaflets 118a, 118b, 118c to be secured to the replacement valve 100 without being covered by a frame or stent structure (e.g., without any open cells 115 surrounding the leaflets 118a, 118b, 118c, or without any open cells 115 positioned between the leaflets 118a, 118b, 118c and the patient's valve). For example, the leaflet-supporting members 116a, 116b, 116c can serve as a boundary for the open cells 115, such that none of the open cells 115 cross or extend beyond the leaflet-supporting members 116a, 116b, 116c to overlap the leaflets 118a, 118b, 118c, contrary to known transcatheter valves. In this manner, the support structure of the valve (usually metal) is substantially separated from the leaflets, thereby allowing the replacement valve 100 to be crimped to a relatively small diameter.

Commissure posts 120 are located between each of the leaflets 118a, 118b, 118c. Conventional replacement valves typically include commissure posts having sharp or abrupt edges that can be less than ideal for contact with a patient's aorta wall or other native tissue. Reinforcement elements 114a, 114b, 114c and leaflet-supporting members 116a, 116b, 116c can substantially prevent contact between sharp commissure points and the aorta wall such as by providing a smooth transition between the reinforcement arcs and commissure posts 120. Further, the reinforcement arcs can increase the strength of commissure posts 120 and can help prevent the commissure posts 120 from collapsing inward when the leaflets 118a, 118b, 118c are loaded (e.g., when subjected to back pressure).

In some embodiments, lower portion 108 and leaflet portion 110 can form a single integral body. In some embodiments, lower portion 108 and leaflet portion 110 can be coupled to one another by connecting elements 124. Connecting elements 124 can be configured as a partial extension of the stent structure 112 of the lower portion 108 and can be coupled to the leaflet-supporting members 116a, 116b, 116c. For example, connecting elements 124 can comprise a cluster of four open cells 115 bridging between the lower portion 108 and the leaflet portion 110. Connecting elements 124 can extend to locations adjacent the commissure posts 120 positioned between adjacent pairs of leaflet-supporting members, but do not extend into the leaflet windows 119 (e.g., do not cross the leaflet-supporting members 116a, 116b, 116c) in some embodiments. In other embodiments, lower portion 108 and leaflet portion 110 are not coupled via connecting elements 124. Thus, lower portion 108 and leaflet portion 110 can be constructed as two separate components which are connectable together (e.g., couplable to one another).

Figure 28:
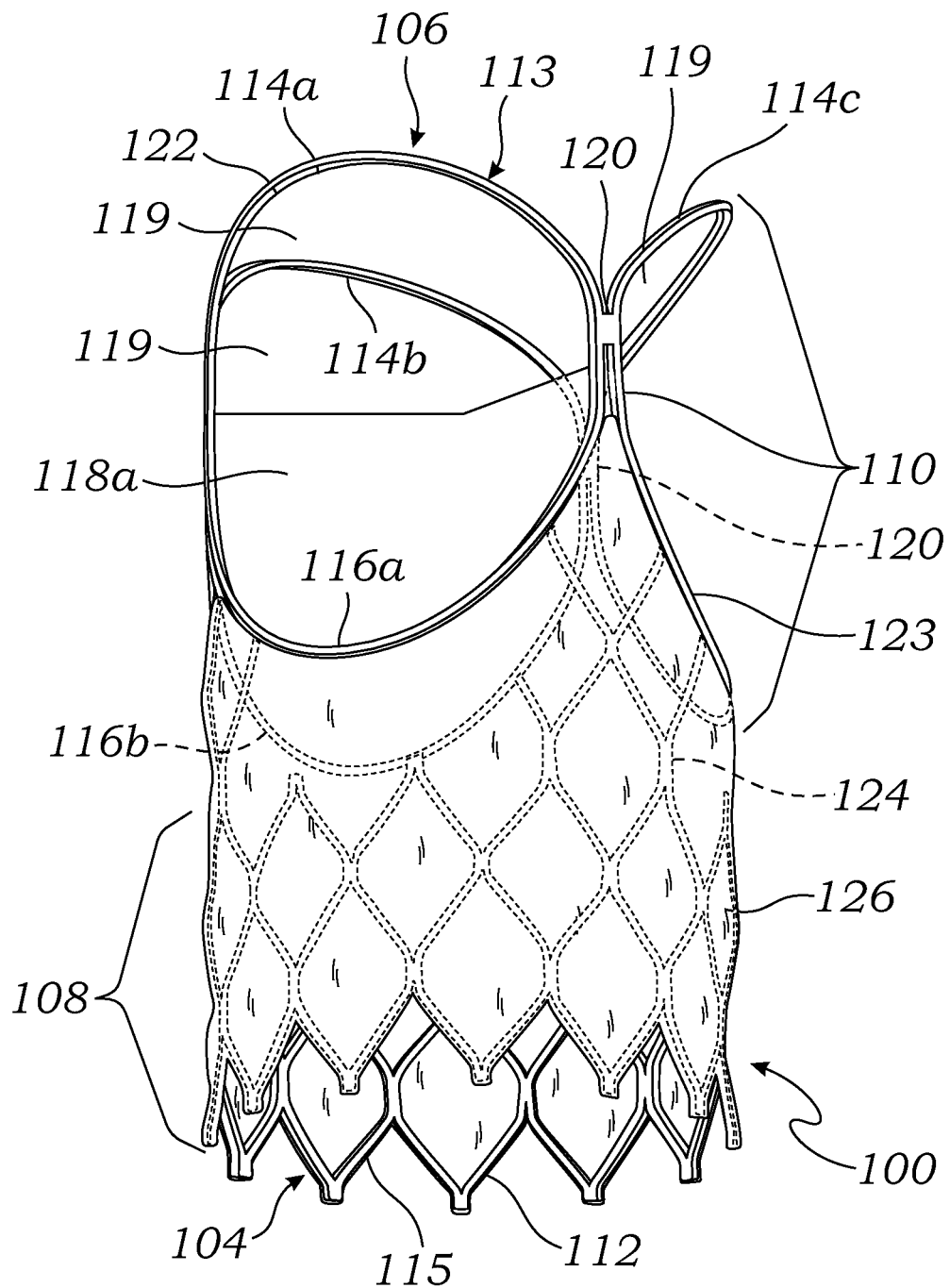
FIG. 28 is a perspective view of one embodiment of a replacement heart valve.

While not shown for clarity in FIGS. 1-3, lower portion 108 can include a flexible sleeve (e.g., a skirt) and/or a sealing component covering at least a portion of the stent structure 112. For example, a polyethylene terephthalate (PET) fabric sleeve can cover at least a portion of the stent structure 112 such that the PET fabric sleeve can reduce or substantially eliminate leakage around the replacement valve 100. One embodiment of a suitable flexible skirt or sealing component 126 is shown in FIG. 28. As seen in FIG. 28, the skirt 126 can cover substantially the entire outer surface of the stent structure 112, thereby reducing or substantially eliminating leakage around the replacement valve 100 (e.g., leakage through the stent structure 112). The skirt 126 can substantially continuously contact and/or follow the contours of one or more components of the leaflet portion 110. For example, as shown in FIG. 28, the skirt 126 can substantially continuously contact and/or follow the contours of the leaflet-supporting members 116a, 116b, 116c, thereby creating substantially continuous sealing around the stent structure 112. In this manner, the skirt 126 can substantially prevent blood from flowing into the stent structure, through the aortic annulus, and back into the left ventricle during diastole.

FIG. 6 shows another embodiment of a replacement heart valve 600 that can be positioned supraannularly. Replacement valve 600 comprises an inflow end 604 and an outflow end 606. When in place within a patient's heart, blood flows into the valve 600 at the inflow end 604 and out of the valve 600 at the outflow end 606. Replacement valve generally includes a lower portion 608 adjacent the inflow end 604 and a leaflet portion 610 adjacent the outflow end 606. Lower portion 608 can serve to keep the native valve open and can be positioned within the native valve annulus. Lower portion 608 can also help to fix or anchor the replacement valve 600 in place with the patient's native valve (e.g., lower portion 608 can be positioned within the native aortic valve). Lower portion 608 can also serve as a basis for anchoring the leaflet portion 610, while the leaflet portion 610 can be positioned supraannularly (e.g., above the native valve annulus).

Lower portion 608 includes a stent structure 612 (e.g., a wire mesh frame) that can comprise, for example, a plurality of open cells 615. Open cells 615 can be differently shaped from one another, with some open cells 615 being enlarged and/or asymmetrical with respect to other open cells 615. While not shown for clarity, lower portion 608 can also include a flexible sleeve (e.g., a fabric sleeve) and/or a sealing component covering at least a portion of the stent structure 612. For example, a PET fabric sleeve can cover at least a portion of the stent structure 612 such that the PET fabric sleeve can reduce or substantially eliminate leakage around the replacement valve 600.

The leaflet portion 610 can include a two-part scalloped frame 613 that comprises reinforcement elements 614a, 614b, 614c and leaflet-supporting members 616a, 616b, 616c. Leaflets can be secured between respective reinforcement elements 614a, 614b, 614c and leaflet-supporting members 616a, 616b, 616c. For example, a leaflet can be secured in place in a gap 617 defined between reinforcement element 614a and leaflet-supporting member 616a. A portion of each of the leaflets can be sandwiched between the reinforcement elements and leaflet-supporting members such that the leaflets can operate (e.g., open and close) within windows 619 defined by the reinforcement elements 614a, 614b, 614c. Such configurations can allow for the leaflets to be secured to the replacement valve 600 without being covered by a frame or stent structure (e.g., without open cells 615 extending into or over the leaflet windows 619). Thus, the diameter of the crimped replacement valve 600 can be kept to a minimum.

Commissure posts 620 are located between each of the leaflets, at the locations where adjacent reinforcement arcs come together (e.g., where reinforcement element 614a and leaflet-supporting member 616a meet reinforcement element 614b and leaflet-supporting member 616b).

Figure 4:
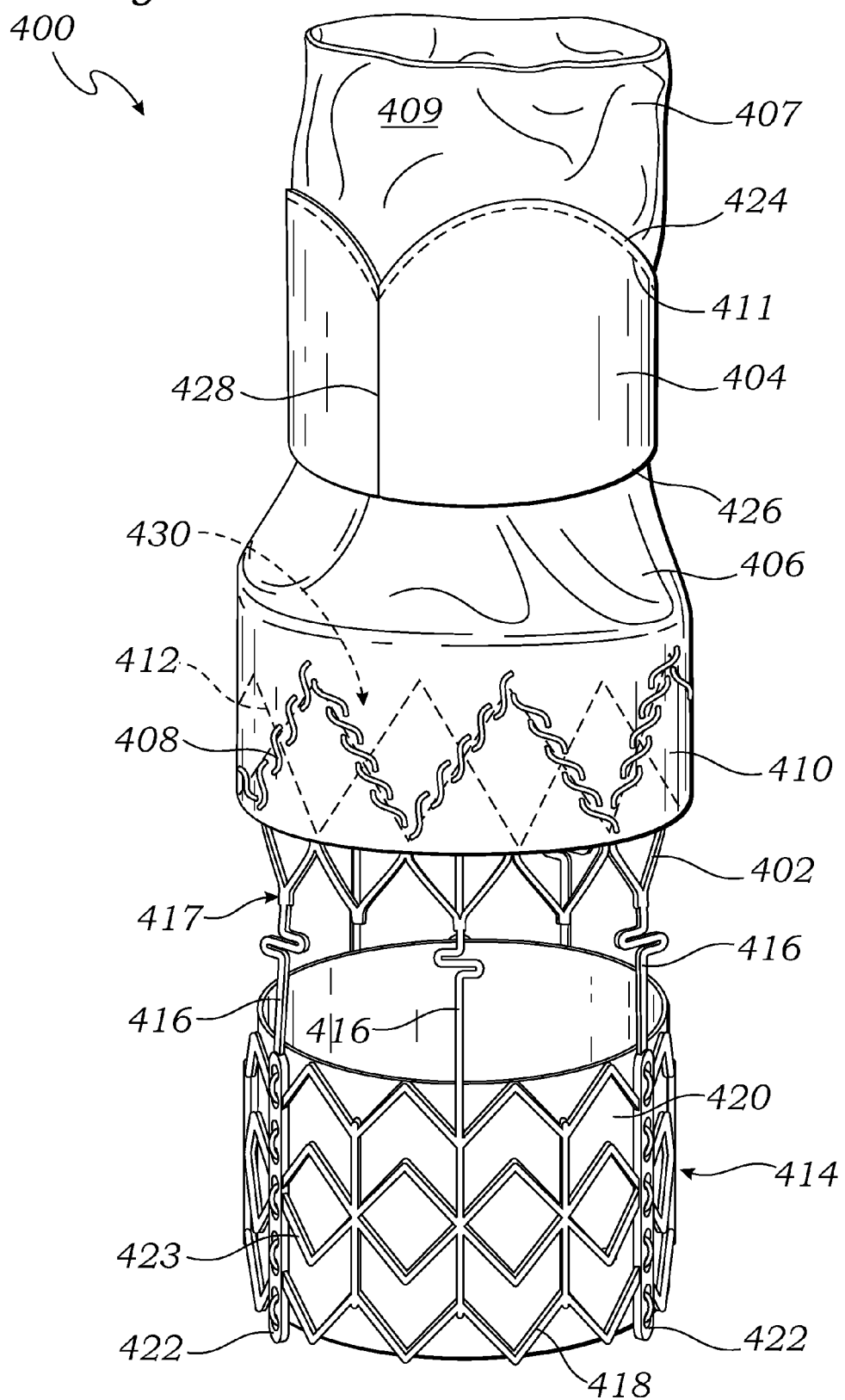
FIG. 4 is a perspective view of another embodiment of a replacement heart valve, in a delivery configuration.

FIGS. 4-5 illustrate another embodiment of a replacement heart valve 400 that can be fully assembled prior to delivery, and transitioned from a delivery position or configuration (FIG. 4) to an operating position or configuration (FIG. 5) once the replacement valve has passed through the narrowest part or parts of the patient's vasculature. Transition from the delivery position to the operating position can be performed, for example while the replacement valve 400 is within the patient's aorta prior to implantation at the native valve. Alternatively, transition from the delivery position to the operating position can be performed after deployment of the replacement valve at the target site (e.g., the native valve annulus).

Replacement valve 400 can include a frame structure, or stent, 402 and leaflets 404. A flexible sleeve 406 (e.g., a PET or Nitinol-PET composite fabric sleeve) can be coupled at one end 410 to the stent 402, such as by sutures 408 (e.g., the inner surface of the flexible sleeve 406 can be coupled to the outer or external surface of the stent 402). The flexible sleeve 406 can also be coupled to the leaflets 404, and can thus allow for separation of the leaflets 404 from the upper end 412 of the stent 402 along the axial direction while the replacement valve is in the delivery configuration. The replacement valve can thus be fully assembled in the delivery configuration, and yet allow for axial separation of the leaflets 404 from the stent 402. Because the leaflets 404 lie entirely outside of the frame structure during delivery of the valve, the valve can be crimped to a very small profile.

The leaflets 404 can each include a first end 424 and a second end 426. The first end 424 can be scalloped and can be coupled to an upper portion 407 of the flexible sleeve 406. In some embodiments, the leaflets 404 can be mounted or coupled to an outer surface 409 of the flexible sleeve 406, such as by sutures 411. The second end 426 of the leaflets 404 can be positioned on the outer surface 409 of the flexible sleeve 406 while in the delivery configuration, but the second end 426 of the leaflets 404 is not secured to the flexible sleeve 406 in some embodiments to allow the leaflets to coapt when placed in the operating configuration (e.g., the second end 426 of the leaflets 404 can be free to move with respect to the flexible sleeve 406).

As shown in FIG. 5, after the replacement valve 400 has been transitioned to its operating configuration, the second ends 426 of the leaflets 404 are free to open and close, and thus are not secured to the flexible sleeve 406 except at the commissures 428.

To transition the replacement valve 400 from the delivery configuration shown in FIG. 4 to the operating configuration shown in FIG. 5, the flexible sleeve 406 can be inverted or flipped outside in (or inside out) by pushing or pulling the upper portion 407 of the sleeve 406 inwardly and downwardly (in FIG. 4) into the stent 402. Thus, a portion 429 of the flexible sleeve 406 can be folded over the upper end 412 of the stent 402 in the operating configuration. As a result of such a transition, the outer surface 409 of the flexible sleeve 406 can be positioned within and facing the interior lumen 430 of the replacement valve 400. Thus, the flexible sleeve 406 can be inverted such that the upper portion 407 of the flexible sleeve 406 is moved to a position within the lumen 430 of the stent 402 (e.g., at a position below the lower end 410 of the flexible sleeve 406).

In some embodiments, a conventional delivery system can be used to transition replacement valve 400 from a delivery configuration to an operating configuration. For example, the flexible sleeve 406 (e.g., the upper portion 407 of the flexible sleeve 406) can be releasably coupled to the delivery system. After deployment (e.g., expansion and/or removal of a restraining sheath) of the stent 402 and/or optional temporary frame 418, the delivery system can be advanced towards the patient's left ventricle, thereby pulling, dragging, or pushing the fabric sleeve 406 into the lumen 430 of the replacement valve 400, and inverting the valve leaflets 404.

During transition, the leaflets 404 can be inverted, such that the second end 426 of the leaflets 404 moves from being below the first end 424 in the delivery configuration to being above the first end 424 in the operating configuration. Further, as a result of transitioning, the leaflets 404, which can be outside of the lumen 430 in the delivery configuration shown in FIG. 4, can be at least partially positioned within (e.g., inside) the lumen 430 of the replacement valve 400 in the operating configuration shown in FIG. 5.

In the operating configuration, both the leaflets 404 and the flexible sleeve 406 can be positioned at least partially inside the lumen 430 of the stent 402. In some embodiments, the flexible sleeve 406 can be stretched down into the lumen 430 of the stent 402, and anchored to the stent 402 (e.g., anchored near the lower end 417 of the stent 402 and/or near the upper end 412 of the stent 402) while in the operating configuration. For example, the flexible sleeve 406 can be secured in place within the lumen 430 of the stent 402 by being coupled to the stent 402 by any suitable attachment structure. In one specific embodiment, an additional stent structure can be arranged to sandwich the flexible sleeve 406 to the stent 402 after the replacement valve 400 has been transitioned to its operating configuration. For example, an additional stent structure can be expanded within the sleeve 406 (e.g., within the lumen 430, near the lower end 417) to push at least a portion of the sleeve 406 against the stent 402, thereby anchoring the sleeve 406 in place in an operating configuration.

Replacement valve 400 can optionally include a temporary valve, such as temporary valve 414 that can be coupled to the stent 412 by, for example, one or more connecting posts 416 extending from the lower end 417 of the stent 402 (e.g., opposite the upper end 412 of stent 402). When included, the temporary valve 414 can operate for a relatively short period of time (e.g., a matter of hours, or less) as a temporary replacement valve during the time between initial deployment of replacement valve 400 in its delivery configuration and the transition to its operating configuration.

Optional temporary valve 414 can include temporary valve frame 418 and temporary valve leaflets 420. Temporary valve frame 418 can, for example, be an annular stent-like structure having a plurality of angularly spaced, vertically extending commissure attachment posts or struts 422. Commissure posts 422 can be positioned between adjacent leaflets 420. Commissure posts 422 can serve as points of attachment between the temporary valve frame 418 and the temporary valve leaflets 420. Commissure posts 422 can be interconnected via one or more rows of circumferentially extending struts 423. The struts 423 in each row can be arranged in a zigzag or generally saw-tooth-like pattern extending in the direction of the circumference of the frame 418 as shown. Temporary valve 414 can be any structure suitable for temporarily serving as a replacement heart valve, and need not have the structure illustrated in FIG. 4. In some embodiments, temporary valve 414 comprises a minimal amount of material.

In some embodiments, after replacement valve 400 is transitioned to its operating configuration, the leaflets 404 and/or flexible sleeve 406 can hold the temporary valve 414 in an open configuration. In such configurations, the open temporary valve (e.g., the open temporary valve leaflets 420) can serve as a skirt or sealer for the replacement valve 400. In some embodiments, the flexible sleeve 406 can be secured to the stent 402 by any suitable attachment structure. In one specific embodiment, an additional stent structure can be arranged to sandwich the flexible sleeve 406 to the stent 402 and/or to the temporary valve frame 418 after the replacement valve 400 has been transitioned to its operating configuration.

In some embodiments, the temporary valve 414 can be removed from the replacement valve 400, such as along with removal of the delivery system used to implant the replacement valve 400. In other embodiments, the temporary valve can remain in place, coupled to the replacement valve 400. In some embodiments, the temporary valve 414 can be resorbable. In some embodiments, the temporary valve can be integral to the replacement valve 400 (e.g., the temporary valve can comprise slits cut through the flexible sleeve 406).

Figure 7:
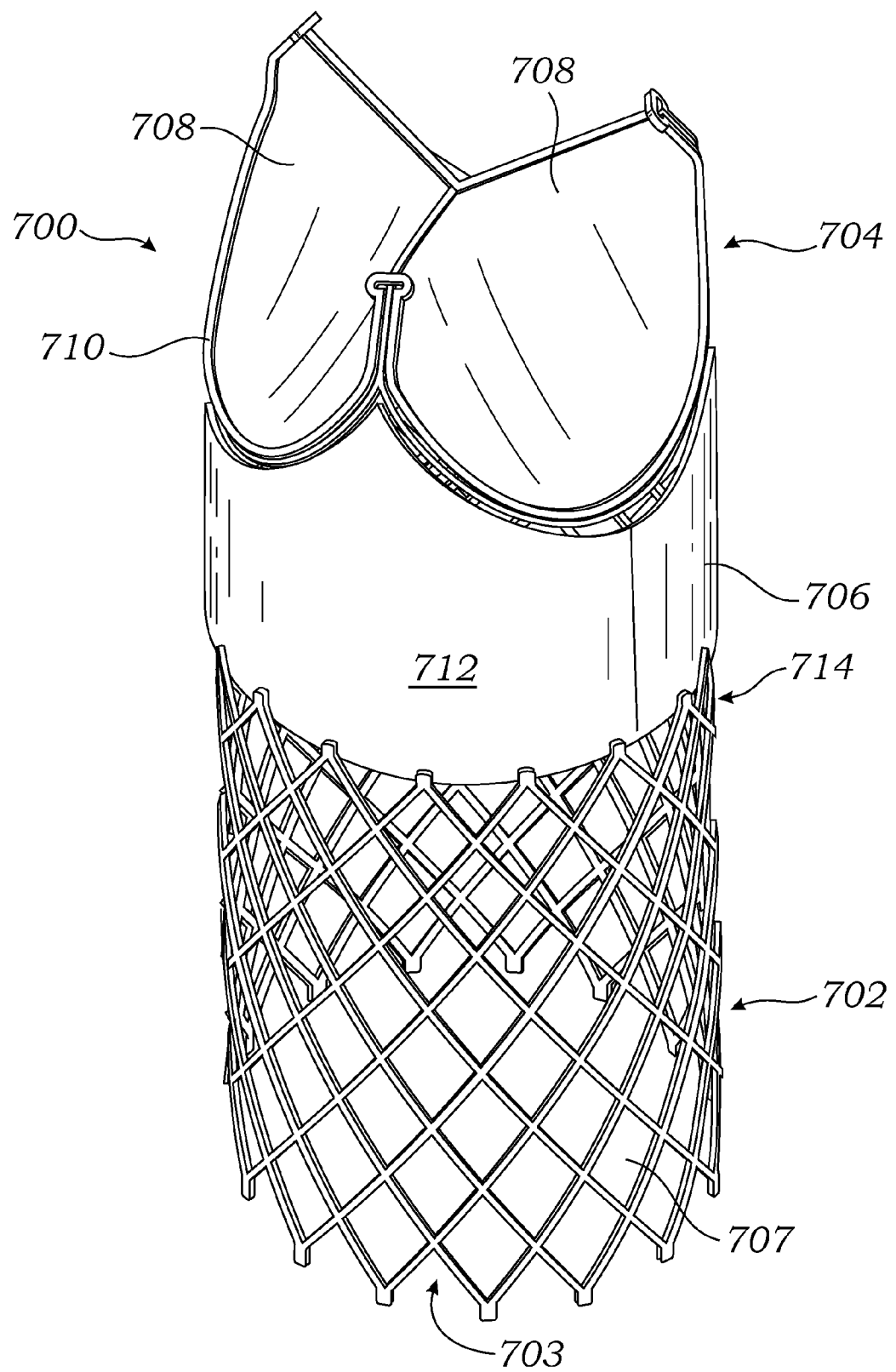
FIG. 7 is a perspective view of one embodiment of a replacement heart valve.

FIGS. 7-8 illustrate another embodiment of a replacement heart valve 700. Replacement valve 700 can be at least partially delivered in a delivery configuration (FIGS. 7 and 8A) and then transitioned to an operating configuration (FIG. 8B).

Replacement valve 700 generally comprises a frame, or stent 702 (e.g., a collapsible stent), a valve portion 704, and a flexible skirt, or sleeve 706 (e.g., a PET fabric sleeve). In one particular embodiment, the stent 702 can comprise interconnected wires or struts that zigzag to create diamond-shaped cells 707 which can facilitate anchoring of the replacement valve 700 within a patient's valve. While cells 707 can be generally diamond-shaped, other shapes of open cells can also be included, such as the irregular open cells 807 shown in FIG. 8C. The flexible sleeve 706 can couple the valve portion 704 to the frame 702. The flexible sleeve 706 can be coupled to the stent 702, such as by being sutured to the stent 702 along an upper portion 714 of the stent 702.

The leaflets 708 of the valve portion 704 can be supported by a slim frame 710, such as the two-part scalloped frame 710 best seen in FIG. 7. Embodiments of the two-part scalloped frame 710 can be provided without, for example, diamond-shaped cells 707. In some embodiments, the two-part scalloped frame 710 does not include any cells other than the window openings for the leaflets 708 (e.g., the two-part scalloped frame 710 can be lacking a portion suitable for anchoring the device in place within the patient's valve). Thus, the leaflets 708 can be attached to a portion of the replacement valve 700 having less material than, for example, the stent 702 portion. In other embodiments, the two-part scalloped frame 710 can comprise a plurality of open cells, but in some embodiments, the open cells do not overlap with the leaflets. For example, FIG. 8C shows a valve portion 800 having a two-part scalloped frame 810 supporting leaflets 808. Open cells 807 can be provided, for example, at the points 811 where adjacent arcs of the two-part scalloped frame 810 meet. As shown in FIG. 8C, however, in some embodiments, the open cells 807 do not extend past the two-part scalloped frame 810, and thus do not overlap with the leaflets 808.

To transition from the delivery configuration (FIGS. 7 and 8A) to an operating configuration (FIG. 8B), the valve portion 704 can be slid into the lumen 703 of stent 702. For example, the replacement valve 700 can be delivered to a patient's valve, such as by being delivered on a catheter through a patient's femoral artery, while the components (e.g., the valve portion 704, the stent 702, and the flexible sleeve 706) are aligned in a stack (i.e., in a row or adjacent to one another in the axial direction along the delivery catheter) to minimize the crimped profile of the replacement valve 700. In some embodiments, the valve portion 704, the stent 702, and the flexible sleeve 706 can form a single integral structure that can be advanced through the patient's vasculature as a single unit. Transition of the replacement valve 700 to an operating configuration can take place at any point after the replacement valve has been delivered past the narrowest points it will travel through in the patient's vasculature (e.g., after traveling through the femoral artery). For example, the replacement valve 700 can be transitioned to an operating configuration while in the abdominal or ascending aorta. In some embodiments, the replacement valve 700 can be transitioned to an operating configuration before, during, or after implantation in the native valve.

FIG. 8A shows a cross section of the replacement valve 700 shown in FIG. 7, shown in a delivery configuration. To transition to the operating configuration shown in FIG. 8B, the valve portion 704 can be pulled or pushed inside the stent 702 (e.g., into the lumen 703 of the stent 702) while the flexible sleeve 706 is inverted and/or folded onto itself. The outer surface 712 of the flexible sleeve in the delivery configuration (FIG. 8A) can thus become an interior surface 712 in the operating configuration (FIG. 8B), facing the lumen 703 of stent 702. In some embodiments, the valve portion 704 can be at least partially crimped while being inserted into the stent 702. In some embodiments, the valve portion 704 can be configured to self-expand after it is released into the lumen 703 of the stent 702. For example, the valve portion 704 can be at least partially restrained (e.g., crimped) by a sheath while it is being positioned inside the stent 702. Once the sheath is removed, the valve portion 704 can self-expand inside the lumen 703 of the stent 702.

Thus, in the operating configuration, both the valve portion 704 and the flexible sleeve 706 can be positioned inside the lumen 703 of the stent 702. In some embodiments, the flexible sleeve 706 can be stretched down into the lumen of the stent 702, and anchored to the stent 702 while in the operating configuration (e.g., anchored to the upper portion 714 of the stent 702). For example, the flexible sleeve 706 can be secured in place within the lumen 703 of the stent 702 by being coupled to the stent 702 by any suitable attachment structure. In one specific embodiment, an additional stent structure can be arranged to sandwich the flexible sleeve 706 to the stent 702 after the replacement valve 700 has been transitioned to its operating configuration. For example, an additional stent structure can be expanded within the sleeve 706 to push the sleeve 706 against the outer stent 702, thereby anchoring the sleeve 706.

FIGS. 9-10 illustrate another embodiment of a replacement valve 900 having a flexible sock, skirt, or sleeve 902 (e.g., a fabric sleeve) that can be inserted into the lumen 903 of a stent portion 904 before, during, or after delivery of the replacement valve 900 to a patient's native valve. FIG. 9 shows the replacement valve 900 in a delivery configuration and FIG. 10 shows the replacement valve 900 in an operating configuration.

The flexible sleeve 902 can extend along substantially the entire length of the replacement valve 900 and can couple the stent portion 904 to a valve portion 910. For example, the flexible sleeve can extend from a lower edge 906 of the stent portion 904 to an upper edge 908 of the valve portion 910 that includes leaflets 912. A lower end 913 of the flexible sleeve 902 can be positioned adjacent an inner surface 914 of the stent portion 904 and coupled to the stent portion 904, such as by sutures 916. The flexible sleeve 902 can be positioned adjacent an outer (e.g., exterior) surface of an upper stent, or frame structure, of the valve portion 910, such that the flexible sleeve 902 at least substantially covers the upper frame structure. Suitable frame structures for the upper stent underlying the flexible sleeve 902 include, for example, the upper stent 800 illustrated in FIG. 8C, as well as the valve portions or leaflet structures from any other disclosed embodiment, or combinations thereof. The flexible sleeve 902 can be coupled to the upper frame structure, such as by sutures 918. The flexible sleeve 902 can be coupled to leaflets 912, such as by sutures 920.

A middle portion 922 of the flexible sleeve 902 can be fabric (or other flexible material) alone, without any underlying frame structures. This can allow for a minimized crimped profile when the replacement valve 900 is crimped onto a delivery device in the delivery configuration shown in FIG. 9. When transitioning to the operating configuration shown in FIG. 10, the valve portion 910 can be pushed or pulled into the lumen 903 of the stent portion 904.

Once the transition is complete, substantially the entire valve portion 910 and flexible sleeve 902 can be positioned within the lumen 903 of the stent portion 904. Thus, the flexible sleeve 902 can be compressed or folded onto itself, and can be substantially positioned between an outer surface up the upper frame and an inner surface of the stent portion 904 in the operating configuration.

FIGS. 11-21 illustrate specific methods of implanting embodiments of a replacement valve (e.g., the replacement valves shown in FIGS. 7-10), using simplified representations for clarity. In one method, shown in FIGS. 11-17, a replacement valve 1100, which is a simplified representation of the valve shown in FIGS. 9-10, can be at least partially transitioned from a delivery configuration to an operating configuration before placement within the native valve.

FIG. 11 shows a replacement valve 1100 in a delivery configuration on a delivery catheter 1102. Replacement valve 1100 can include a stent, or frame portion 1104 that is crimped onto a balloon 1106. In other embodiments, the stent portion 1104 can be self-expandable. Replacement valve 1100 can also include a valve portion 1108 that is crimped onto the delivery catheter shaft 1102 at a location spaced away from the stent portion 1104, along the length of the delivery catheter 1102 (e.g., the valve portion 1108 can be separated from the stent portion 1104 along the axial direction of the delivery catheter 1102). The valve portion 1108 can be coupled to the stent portion 1104 by a flexible sleeve 1110. The replacement valve 1100 can then be inserted into the body (e.g., at the femoral artery) and navigated through a patient's vasculature to a suitable location, such as to the abdominal aorta, to begin transitioning the valve to its operating configuration. Any location within the vasculature that can allow for the partial (e.g., tapered) expansion of the stent portion as described below in connection with FIGS. 11-17 is suitable.

As shown in FIG. 12, once the replacement valve 1100 has been navigated through the narrowest parts of the patient's vasculature, the replacement valve can begin to be transitioned from the delivery configuration to the operating configuration. In one embodiment, the stent portion 1104 can be partially expanded (e.g., by at least partially inflating a balloon 1106 that is positioned on the delivery catheter under at least a portion of the stent portion 1104) while in, for example, the patient's abdominal or ascending aorta. The balloon 1106 can be configured to partially expand the stent portion 1104 to form a tapered shape as shown, by, for example, positioning the stent portion such that one end 1116 is mounted off of the balloon 1106. The stent portion 1104 can be partially expanded enough to allow for at least partial insertion of the valve portion 1108 into the lumen of the stent portion 1104. The balloon 1106 can then be deflated, as shown in FIG. 13, to facilitate transitioning of the replacement valve 1100 from the delivery configuration to the operating configuration.

Figure 14:
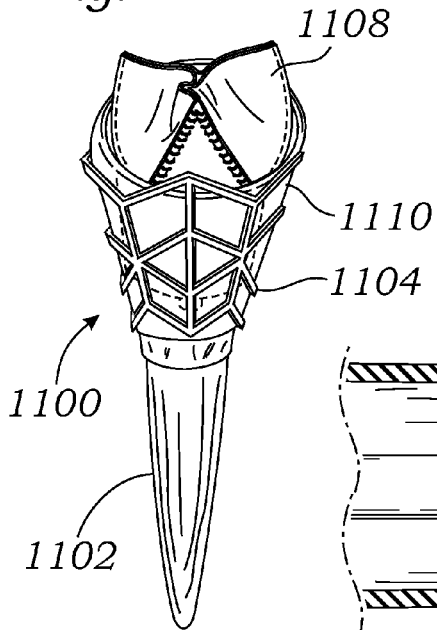
FIG. 14 is a perspective view of the valve portion of a replacement heart valve being pushed into the stent portion of the replacement valve.
Figure 15:
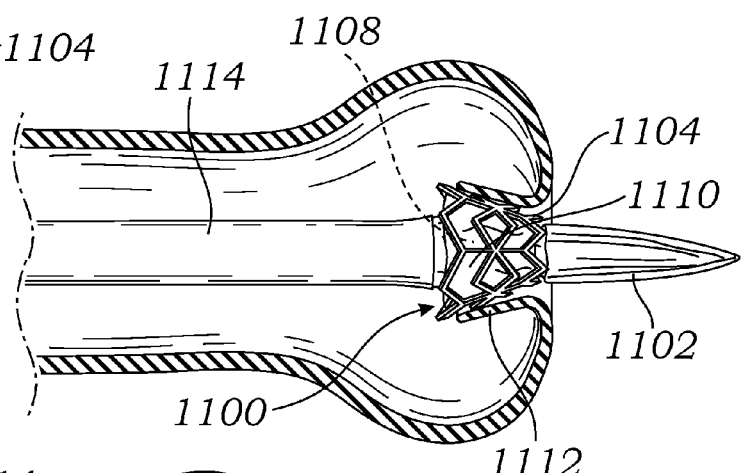
FIG. 15 is an elevation view of a replacement heart valve being positioned within a patient's native valve annulus.
Figure 16:
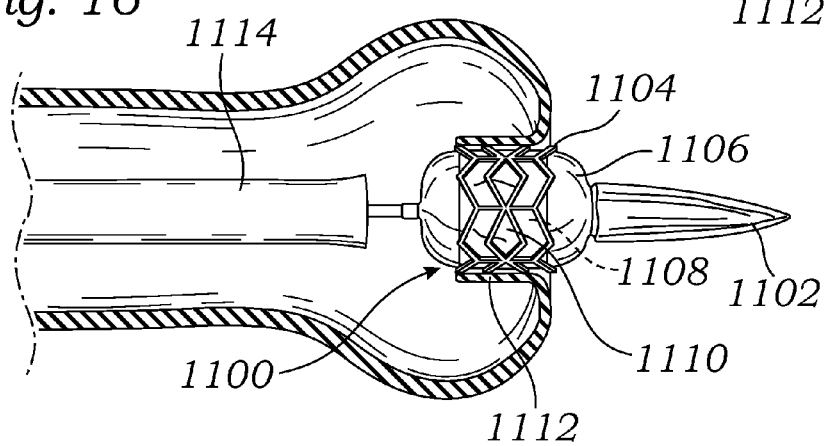
FIG. 16 shows an elevation view of the replacement heart valve of FIG. 15 being fully expanded within the native valve annulus by an inflated balloon.
Figure 17:
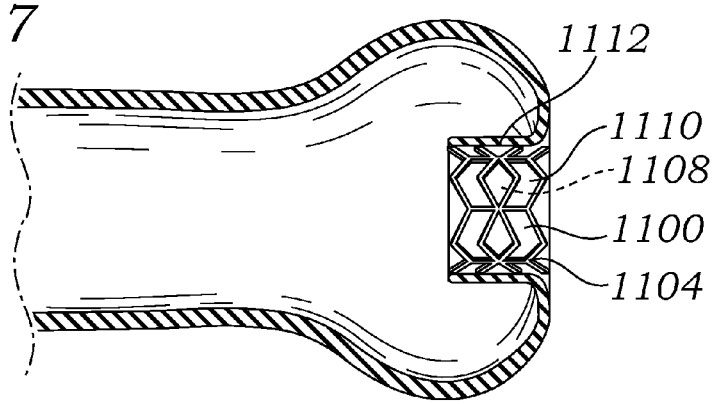
FIG. 17 shows an elevation view of a replacement heart valve in place in a native valve after deployment is complete.

Once the balloon 1106 is deflated, the valve portion 1108 (which can be at least partially crimped) can be pushed into the lumen of the stent portion 1104, such as by pushing an outer shaft 1114 against the valve portion 1108 in the distal direction. FIG. 14 illustrates the mating of the stent portion 1104 to the valve portion 1108 (the rest of the delivery catheter 1102 and outer shaft 1114 are not shown in FIG. 14, for clarity). In FIG. 14, the valve portion 1108 has been partially inserted into the lumen of the stent portion 1104. FIGS. 15-17 show the valve portion 1108 fully inserted into the lumen of the stent portion 1104.

The flexible sleeve 1110 can be configured to limit the motion of the valve portion 1108 such that the flexible sleeve 1110 stops the valve portion 1108 from being pushed too far into the stent portion 1104. The flexible sleeve 1110 can be sized and designed to provide for the desired positioning of the valve portion 1108 within the stent portion 1104. At this stage, the valve portion 1108 and the stent portion 1104 are both positioned on the balloon 1106 (not visible in FIG. 14).

Once the replacement valve 1100 has been transitioned to its operating configuration, the replacement valve 1100 can then be navigated further and positioned within the native valve annulus 1112, as shown in FIG. 15. The steerable outer shaft 1114 can facilitate positioning of the replacement valve 1100 within the native valve annulus, and can then be moved (e.g., the outer shaft 1114 can be retracted slightly as shown in FIG. 16), so as not to interfere as the replacement valve 1100 is further expanded. Rapid pacing can be performed, as is known in the art. As shown in FIG. 16, the balloon 1106 can be inflated to fully expand the replacement valve 1100 (e.g., the valve portion 1108 and the stent portion 1104 can be expanded together, at the same time). Balloon 1106 can then be deflated, rapid pacing can be stopped, and the delivery catheter 1102 can be removed from the patient. FIG. 17 shows the replacement valve 1100 in an operating configuration (e.g., with the valve portion 1108 positioned inside the lumen of the stent portion 1104) within the patient's native valve annulus 1112.

In some embodiments, a replacement valve can be transitioned to an operating configuration during implantation at the native valve site, rather than before positioning at the native valve site (e.g., the replacement valve can be transitioned to its operating configuration once at least part of the replacement valve has been positioned in the native valve). For example, FIGS. 18 to 21 illustrate one such method. In this method, a replacement valve 1800 having a stent portion 1804 and a valve portion 1808 can be crimped onto a delivery catheter 1802. As shown in FIG. 18, the replacement valve 1800 can be navigated to the implantation site and positioned, such that the replacement valve 1800 is at least partially positioned within the native valve annulus 1812 in its crimped state on the delivery catheter 1802. Thus, at least part of the stent portion 1804 is positioned to engage with the native valve (e.g., positioned such that at least part of the stent portion 1804 contacts the valve annulus 1812, once the stent portion 1804 is expanded).

As shown in FIG. 19, the stent portion 1804 can then be expanded to its functional size (e.g., by a balloon, or the stent can be self-expanding), while at least a portion of the flexible sleeve 1810 and the valve portion 1808 remain crimped on the delivery catheter 1802. The stent portion 1804 can be expanded to a diameter sufficient to engage the native valve annulus 1812, thereby anchoring the replacement valve 1800.

In some embodiments, the flexible sleeve 1810 can be provided with one or more slits or cutouts 1814 that can serve as temporary leaflets that allow blood to flow through the replacement valve 1800 while it is being implanted. Rapid pacing can be performed, as is known in the art. Once the stent portion 1804 has been expanded and is engaged with the native valve annulus 1812, the balloon 1806 can be deflated. This allows room within the lumen of the stent portion 1804 for the valve portion 1808 and the flexible sleeve 1810 to be inserted, thus facilitating transitioning of the replacement valve 1800 from the delivery configuration (FIGS. 18-19) to the operating configuration (FIGS. 20-21).

FIG. 20 shows the replacement valve 1800 after the valve portion 1808 has been pushed and expanded into (e.g., by balloon or self-expansion) the expanded stent portion 1804. A flex catheter 1816 can be used to push the valve portion 1808 and position it within the stent portion 1804, on the balloon 1806. The flexible sleeve 1810 can be inserted inside the lumen of the stent portion 1804 as the valve portion 1808 is being inserted. The flexible sleeve 1810 can be designed to serve as a stopper, to prevent the valve portion 1808 from being pushed too far into the stent portion 1804. At least a portion of the flexible sleeve 1810 is thus positioned between the inner surface of the stent portion 1804 and the outer surface of the valve portion 1808.

The flex catheter 1816 can be at least partially retrieved and the balloon 1806 can be inflated, as shown in FIG. 21. Inflation of the balloon 1806 can expand the valve portion 1808 until it engages with and/or is coupled to the stent portion 1804, such as by friction. Once the replacement valve 1800 has thus been transitioned to an operating configuration, the balloon 1806 can be deflated, rapid pacing can be stopped, and the delivery system (e.g., delivery catheter 1802) can be removed from the patient.

Figure 22:
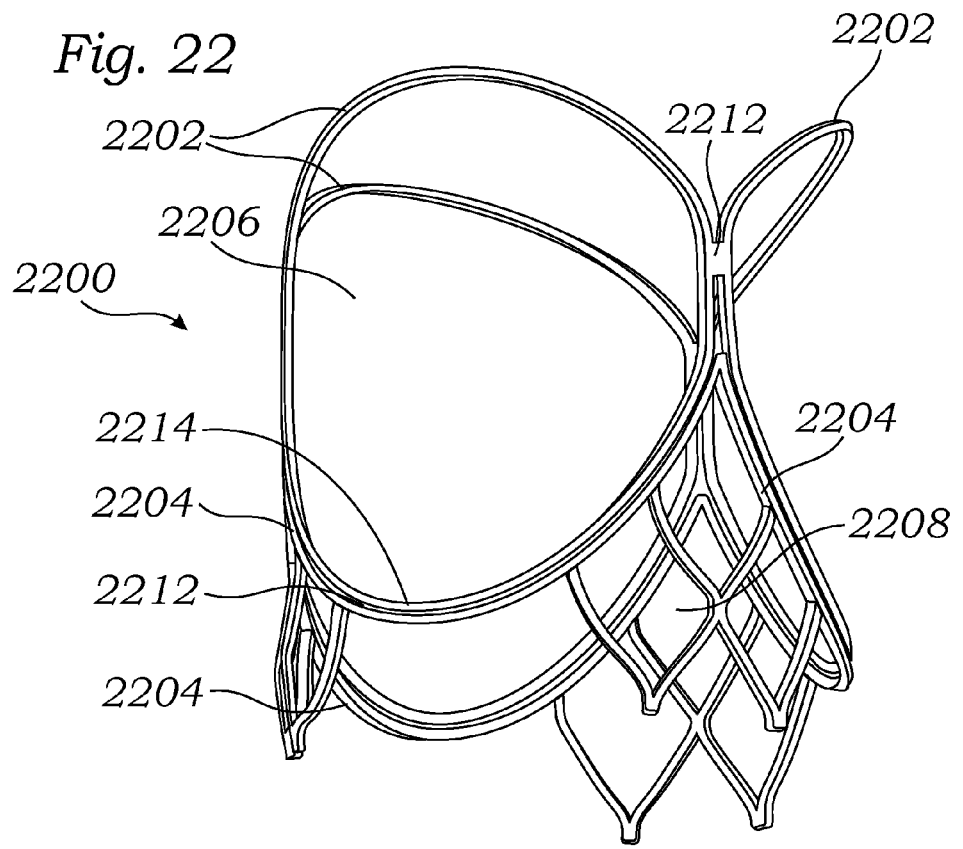
FIG. 22 is a perspective view of one embodiment of a valve portion of a replacement heart valve.

FIG. 22 illustrates another embodiment of an upper stent or frame 2200 that can be incorporated into any of the embodiments described. Frame 2200 can include reinforcement elements 2202 that can serve to define windows 2206 for leaflets. Leaflet-supporting members 2204 can be positioned with respect to the reinforcement elements 2202 to secure the leaflets in place within the windows 2206. For example, a gap 2212 can be created between a lower portion 2214 of the reinforcement elements 2202 and the leaflet-supporting members 2204, and a portion of a leaflet can be inserted into each gap 2212. The reinforcement elements 2202 and leaflet-supporting members 2204 can be arranged to form an upper frame 2200, such as the generally duckbill shaped upper frame 2200 shown in FIG. 22.

Frame 2200 can optionally include open cells 2208 between some or all of the adjacent leaflet-supporting members 2204. Additionally or alternatively, the frame 2200 can optionally include a lower rail 2210 extending around the circumference of the lower portion of the frame 2200. Adjacent reinforcement elements 2202 can be coupled by commissure posts 2212. Commissure posts 2212 can be designed, in some embodiments, to lack sharp, abrupt edges, thus providing a smooth surface. In some embodiments, the upper frame 2200 can be configured to contact the native valve tissue when implanted, while in other configurations, the upper frame 2200 can be configured such that a gap exists between the reinforcement elements 2202 and the valve or vessel wall.

Figure 23:
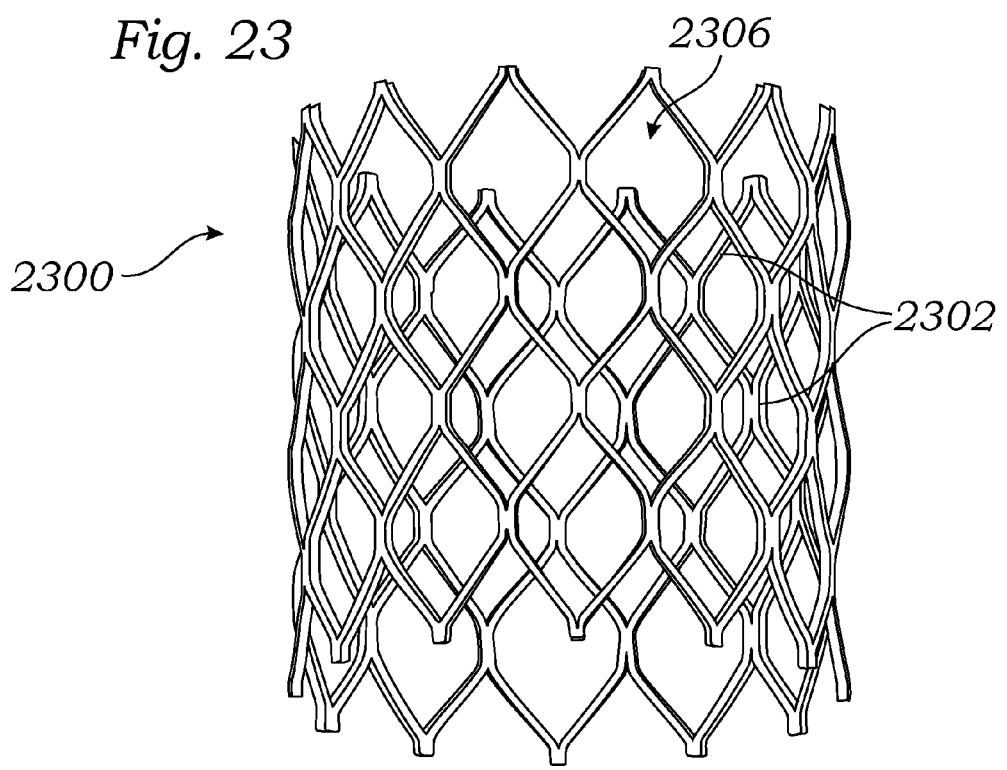
FIG. 23 is a perspective view of one embodiment of a stent portion of a replacement heart valve.

FIG. 23 illustrates one embodiment of a lower stent or frame 2300 that can be incorporated into any of the embodiments described. Frame 2300 can, for example, comprise a wire mesh of cells 2302 arranged in, for example, a substantially cylindrical tube. Frame 2300 can optionally include a circumferential rail 2304 extending around a lower portion of the frame 2300.

Frame 2200 (FIG. 22) and frame 2300 (FIG. 23) can form the two components of a two-part replacement valve. Frame 2200 can be positioned within the lumen 2306 of frame 2300, and rails 2210 and 2304 can be designed to interlock with one another to secure the two frames 2200, 2300 together. In other embodiments, such as the embodiment described more fully below with reference to FIG. 26, a longitudinal rail extending along the axis of frames 2200 and 2300 can connect the two frames and allow for frame 2200 to slide into the lumen 2306 of frame 2300. In alternative embodiments, frame 2200 and frame 2300 can be coupled to one another, such as by connecting posts that extend between frame 2200 and frame 2300. Either or both of frame 2200 and frame 2300 can also be included in embodiments comprising flexible (e.g., fabric) sleeves, described above.

FIGS. 24-25 illustrate another embodiment of a replacement heart valve 2400 that can be transitioned from a delivery configuration (FIG. 24) to an operating configuration (FIG. 25). Replacement valve 2400 can comprise a stent 2402 and leaflets 2404. Each leaflet 2404 can be secured to a U-shaped support rod 2406. In the delivery configuration (FIG. 24), the leaflets 2404 and support rods 2406 are outside of the stent 2402, coupled to a first end 2408 of the stent 2402, such as by attachment points 2410. Attachment points 2410 can be individual hinge points for each of the leaflets 2404. Hinges or equivalent mechanisms can be used to couple the ends of rods 2406 to the upper end of the stent 2402. In alternate embodiments, the attachment points 2410 can comprise a single annular ring extending around the circumference of the stent 2402, adjacent the first end 2408 of the stent 2402. In some embodiments, the attachment points 2410 can comprise narrowed transitional segments that can allow the attachment points 2410 to easily deform or fold. Additionally or alternatively, the support rods 2406 can be coupled to the stent 2402 by secondary attachment means, such as one or more sutures or wires.

To transition to the operating configuration (FIG. 25), the leaflets 2404 and support rods 2406 can be flipped (e.g., inverted), rotated, or bent inwards (e.g., into the lumen 2412 of the stent 2402) so that the leaflets 2404 and support rods 2406 are positioned at least partially within the lumen 2412 of the stent 2402. For example, in some embodiments, the attachment points 2410 can bend approximately 180 degrees to allow inversion and/or eversion of the leaflets 2404 and support rods 2406. In some embodiments, the attachment points 2410 can be configured to twist as the heart valve 2400 is being transitioned to the operating configuration. In some embodiments, the heart valve 2400 can be transitioned to the operating configuration without requiring deformation of the attachment points 2410. For example, in some embodiments, hinges can allow for inversion and/or eversion of the support rods 2406 and leaflets 2404 without requiring deformation of any metallic components. In some embodiments, the leaflets 2404 and support rods 2406 can be flipped inside the stent 2402 after the stent 2402 is radially expanded (e.g., after the stent 2402 is radially expanded within the native valve annulus).

In some embodiments, the replacement valve 2400 can include a locking mechanism (e.g., a snap fit locking mechanism) to prevent the leaflets 2404 and support rods 2406 from repositioning back outside of the stent 2402. For example, in one specific embodiment, one or more lower latches can be positioned within the stent 2402 and configured to capture (e.g., engage with) the support rods 2406 and/or the attachment points 2410 in order to ensure proper positioning of the support rods 2406 and leaflets 2404, and to prevent the heart valve from transitioning back to the delivery configuration shown in FIG. 24. In some embodiments, the support rods 2406 and leaflets 2404 can be bi-stable, such that they are stable both when positioned outside of the stent 2402 in the delivery configuration and stable when positioned inside of the stent 2402 in the operating configuration.

FIG. 26 illustrates a two-part replacement heart valve 2600 that comprises a leaflet portion 2602 and a frame portion 2604 separated from one another along the axial direction. The leaflet portion 2602 and the frame portion 2604 can thus be mounted separately from one another on a delivery catheter (see FIG. 27), thereby reducing the overall diameter (e.g., profile) of the crimped replacement valve because the two portions need not be crimped on top of one another for delivery. The two-part replacement valve 2600 can be pushed through a delivery sheath in a serial fashion, thus reducing the profile of the device. In some embodiments, the two parts (e.g., the leaflet portion 2602 and the frame portion 2604) of the two-part replacement valve can be coupled to one another during the entire delivery process. In other embodiments, the two parts can be separate from one another, and coupled together later during the delivery.

In one embodiment, the leaflet portion 2602 can be coupled to the frame portion 2604, for example, inside the descending aorta. In some embodiments, the leaflet portion 2602 can be pushed or pulled inside the frame portion 2604 by an expandable balloon that is part of the delivery system. The leaflet portion 2602 can be coupled to and/or docked within the frame portion 2604 by any suitable manner, such as, for example, rails, anchors, hooks, friction, interlocking components, and etc. In one specific embodiment, one or more upper longitudinal rails 2606 that are secured to the leaflet portion 2602 can be slid into and/or engaged with respective one or more lower longitudinal rails 2608 that are secured to the frame portion 2604 to couple the leaflet portion 2602 to the frame portion 2604. Longitudinal rails 2606, 2608 can be configured to engage with one another such that longitudinal rails 2606 can slide back and forth along longitudinal rails 2608 along the axial direction.

In some embodiments, the leaflet portion 2602 and the frame portion 2604 are coupled to each other (e.g., coupled via upper and lower rails 2606, 2608) during navigation through the patient's vasculature, and the two parts can be moved relative to one another once in place in or near the native valve annulus. For example, the two-part replacement valve 2600 can be delivered to or near a target site while the leaflet portion 2602 and the frame portion 2604 are coupled to one another by rails 2606, 2608, yet separated from one another in the axial direction. The upper rails 2606 of the leaflet portion 2602 can be slid along the lower rails 2608 of the frame portion 2604 to insert the leaflet portion 2602 within the lumen 2610 of the frame portion 2604.

In some embodiments of delivering replacement valve 2600, the delivery system (e.g., a FlexCath®), leaflet portion 2602, and frame portion 2604 can individually be pushed through a sheath in a serial manner.

FIG. 27 illustrates the replacement valve 2600 shown in FIG. 26 crimped onto a delivery system 2700. The replacement valve 2600 (e.g., the frame portion 2604 and the leaflet portion 2602) can be crimped onto the delivery system 2700 at a location separated axially from a balloon 2702. Thus, in some embodiments, no part of the replacement valve 2600 is mounted or crimped onto the balloon 2702 during initial navigation through the patient's vasculature. This can help to keep the crimped profile of the replacement valve 2600 and delivery system 2700 to a minimum. Embodiments of suitable delivery systems are described further in U.S. Patent Application Nos. 61/170,065 and 61/179,311, which are hereby incorporated herein by reference, in their entirety.

The leaflet portion 2602 can be crimped onto delivery system 2700 at a position separated axially from the frame portion 2604. The leaflet portion 2602 can be coupled to the frame portion 2604, such as by longitudinal rails 2606, 2608. The rails 2606, 2608 can help to keep the leaflet portion 2602 properly aligned with the frame portion 2604, and/or the rails 2606, 2608 can be configured to facilitate movement of the leaflet portion 2602 into the lumen of the frame portion 2604 at the appropriate time.

Delivery system 2700 can comprise a nose piece 2704 and an optional foam piece 2706 disposed on a guidewire shaft 2708 inside the balloon 2702. The balloon 2702 can include a split near a proximal end 2710 of the balloon 2702 (e.g., adjacent the replacement valve 2600) that can be configured to allow a tapered expansion of at least a portion of balloon 2702 in order to facilitate positioning the replacement valve 2600 on the balloon 2702. For example, after navigation to a suitable location within a patient's vasculature, the balloon 2702 can be partially inflated and then retracted so that the leaflet portion 2602 is pushed or pulled at least partially into the lumen of the frame portion 2604 by the at least partially inflated balloon 2702. As the leaflet portion 2602 is being pushed into the frame portion 2604, the upper longitudinal rails 2606 move along the lower longitudinal rails 2608.

When the leaflet portion 2602 is positioned at least partially within the frame portion 2604, the balloon 2702 can be deflated. Then, both the leaflet portion 2602 and the frame portion 2604 can be positioned on the balloon 2702 at the target site, such as by pushing an outer catheter 2712 against the proximal end of the frame portion 2604 to move the entire valve 2600 onto the balloon. The valve 2600 can be positioned over the foam core 2706, which can help retain the valve in place on the balloon while the valve is moved to the deployment site. Once the valve is positioned within the native valve annulus, the balloon 2702 can be fully expanded so as to expand the leaflet portion 2602 and the frame portion 2604 together and anchor them into place within the native valve annulus.

While some disclosed embodiments have been illustrated as having a scalloped frame supporting the valve leaflets, other configurations are also suitable. For example, stents having any shaped cells can be included in the disclosed embodiments.

Any of the disclosed embodiments can be provided with a self-expanding (e.g., comprising Nitinol) lower stent and/or leaflet support frame. Some embodiments include a balloon-expandable stent and/or valve portion. A self-expanding stent can be crimped or otherwise compressed into a small tube and possesses sufficient elasticity to spring outward by itself when a restraint such as an outer sheath is removed. In contrast, a balloon-expanding stent is typically made of a material that is substantially less elastic, and indeed must be plastically expanded from the inside out when converting from a compressed diameter to an expanded diameter. It should be understood that the term balloon-expandable stents encompasses plastically-expandable stents, whether or not a balloon is used to actually expand it. The material of the stent plastically deforms after application of a deformation force such as an inflating balloon or expanding mechanical fingers. Suitable materials for the stent, frame, or reinforcement arc structures of disclosed embodiments include stainless steel, Nitinol, titanium, cobalt, chromium, nickel-based alloys (e.g., a nickel-cobalt-chromium alloy such as MP35N™) polymers, and combinations and alloys thereof. Any other materials that are rigid enough to impart the desired shape to the structures are also suitable.

As described above, some embodiments of a replacement heart valve include a flexible sleeve or skirt. The flexible sleeve can comprise any material that can allow transformation of the replacement valve from the delivery configuration to the operating configuration. Suitable materials include, for example, polyethylene terephthalate (PET) (e.g., Dacron®), silicone, woven polyesters, polytetrafluoroethylene (PTFE), combinations thereof, or other similar materials. In some embodiments, the flexible sleeve can be sutured to the stent portion and/or to the valve portion of the replacement valve.

In other embodiments, the sleeve can be formed by dip coating the replacement valve in a liquefied material, such as liquefied silicone or other similar materials.

Leaflets can be formed of, for example, bovine pericardial tissue, biocompatible synthetic materials, or various other suitable natural or synthetic materials as known in the art and described in U.S. Pat. No. 6,730,118, which is incorporated by reference herein.

Any of the disclosed embodiments of a replacement heart valve can be configured to be positioned and anchored in place within a native valve and/or vessel by outward force of the replacement valve on the valve annulus and/or vessel wall, when in the operating configuration. Thus, in some embodiments, no other anchoring mechanism or structure is present. In alternative embodiments, a replacement valve can include one or more anchoring mechanisms (e.g., hooks, anchors, barbs) to aid in anchoring the replacement valve.

Any of the disclosed embodiments of a replacement heart valve can optionally include one or more radiopaque markers that can facilitate navigation and tracking of the replacement valve through a patient's vasculature during delivery, transforming the valve from a delivery configuration to an operating configuration, and/or positioning and implanting the replacement valve at the target site (e.g., the native valve annulus). For example, one or more radiopaque markers can be coupled to the stent and/or leaflet support frame of a replacement valve. In some embodiments, radiopaque material can be incorporated with the material used to form the replacement valve.

Although the operations of exemplary embodiments of the disclosed methods are described in a particular, sequential order for convenient presentation, it should be understood that disclosed embodiments can encompass an order of operations other than the particular, sequential order disclosed. For example, operations described sequentially may in some cases be rearranged or performed concurrently. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of implanting a replacement heart valve, comprising:
    mounting the replacement heart valve onto a delivery system in a delivery configuration, the replacement heart valve comprising a radially-expandable metallic stent portion, a valve portion, and a plurality of metallic longitudinal rails connecting the valve portion to the stent portion, wherein the stent portion comprises an outer surface and an inner surface defining a lumen, wherein the valve portion comprises a plurality of leaflets formed of pericardial tissue, and wherein, in the delivery configuration, at least a portion of the leaflets are positioned outside of the lumen defined by the stent portion;
    advancing the replacement heart valve to an implant position adjacent a heart valve annulus;

transitioning the replacement valve from the delivery configuration to an operating configuration by sliding the valve portion along the plurality of longitudinal rails for advancing the valve portion relative to the stent portion and positioning the valve portion within the lumen of the stent portion;

radially expanding the stent portion and the valve portion together to cause the stent portion to engage the heart valve annulus, thereby anchoring the replacement heart valve in position within the heart valve annulus; and partially inflating a balloon for engaging the valve portion and pulling the valve portion along the plurality of rails toward the stent portion with the balloon partially inflated.

2. The method according to claim 1, further comprising removing the delivery system from the replacement valve, wherein transitioning the replacement valve from the delivery configuration to the operating configuration occurs prior to removing the delivery system from the replacement valve.

3. The method of claim 1, wherein, in the delivery configuration, the entire valve portion is positioned outside of the lumen defined by the stent portion.

4. The method of claim 1, wherein the act of transitioning the replacement valve from the delivery configuration to the operating configuration occurs after advancing the replacement heart valve to the implant position.

5. The method according to claim 1, wherein the plurality of rails comprises upper rails coupled to the valve portion and lower rails coupled to the stent portion and wherein the upper and lower rails move relative to each other when sliding the valve portion into the lumen of the stent portion.

6. The method of claim 5, wherein the upper and lower rails move relative to each other by sliding by each other axially when sliding the valve portion into the lumen of the stent portion.

7. The method according to claim 1, wherein the valve portion and stent portion are coupled together by the plurality of rails while the replacement heart valve is advanced toward the heart valve annulus.

8. The method according to claim 7, wherein at least the stent portion of the replacement heart valve is crimped onto the delivery system at a location separated axially from the balloon during advancement toward the heart valve annulus.

9. A method of implanting a replacement heart valve, comprising:

mounting the replacement heart valve onto a delivery system in a delivery configuration, the replacement heart valve comprising a radially-expandable metallic stent portion, a valve portion, and a plurality of metallic longitudinal rails connecting the valve portion to the stent portion, wherein the stent portion comprises an outer surface and an inner surface defining a lumen, wherein the valve portion comprises a plurality of leaflets formed of pericardial tissue, and wherein, in the delivery configuration, at least a portion of the leaflets are positioned outside of the lumen defined by the stent portion;

advancing the replacement heart valve to an implant position adjacent a heart valve annulus;

transitioning the replacement valve from the delivery configuration to an operating configuration by sliding the valve portion along the plurality of longitudinal rails for advancing the valve portion relative to the stent portion and positioning the valve portion within the lumen of the stent portion;

radially expanding the replacement heart valve to cause the stent portion to engage the heart valve annulus, thereby anchoring the replacement heart valve in position within the heart valve annulus;

wherein the valve portion and stent portion are coupled together by the plurality of rails while the replacement heart valve is advanced toward the heart valve annulus;

wherein at least the stent portion of the replacement heart valve is crimped onto the delivery system at a location separated axially from a balloon during advancement toward the heart valve annulus;

partially inflating the balloon for engaging the valve portion and pulling the valve portion along the plurality of rails toward the stent portion with the balloon partially inflated; and deflating the balloon and then advancing the replacement heart valve relative to the balloon such that both the stent portion and the valve portion are positioned on the balloon before the step of radially expanding the replacement heart valve.

10. The method of claim 9, comprising deflating the balloon after pulling the valve portion toward the stent portion.

11. The method of claim 9, comprising deflating the balloon after both pulling the valve portion toward the stent portion and positioning at least a portion of the leaflets inside of the lumen defined by the stent portion.

12. The method of claim 9, further comprising inflating the balloon for radially expanding the replacement heart valve to cause the stent portion to engage the heart valve annulus.

13. The method of claim 12, wherein the act of inflating the balloon for radially expanding the replacement heart valve occurs after positioning at least a portion of the leaflets inside the lumen defined by the stent portion.

14. The method of claim 12, wherein the act of inflating the balloon for radially expanding the replacement heart valve occurs after positioning the valve portion inside the lumen defined by the stent portion.

* * * * *